(12) United States Patent
Shadduck

(10) Patent No.: US 8,048,155 B2
(45) Date of Patent: Nov. 1, 2011

(54) INTRAOCULAR IMPLANT DEVICES

(75) Inventor: John H. Shadduck, Tiburon, CA (US)

(73) Assignee: PowerVision, Inc., Belmont, CA (US)

( * ) Notice: Subject to any disclaimer, the term of this patent is extended or adjusted under 35 U.S.C. 154(b) by 0 days.

(21) Appl. No.: 10/358,038

(22) Filed: Feb. 3, 2003

(65) Prior Publication Data

US 2003/0149480 A1 Aug. 7, 2003

Related U.S. Application Data

(60) Provisional application No. 60/353,847, filed on Feb. 2, 2002, provisional application No. 60/362,303, filed on Mar. 6, 2002, provisional application No. 60/378,600, filed on May 7, 2002, provisional application No. 60/405,471, filed on Aug. 23, 2002, provisional application No. 60/408,019, filed on Sep. 3, 2002, provisional application No. 60/431,110, filed on Dec. 4, 2002.

(51) Int. Cl.
  *A61F 2/16* (2006.01)
(52) U.S. Cl. ........................... 623/6.37; 623/6.13
(58) Field of Classification Search ........ 623/6.23–6.31, 623/6.13, 6.22, 6.37, 6.34, 6.4, 6.43, 6.5, 623/6.59

See application file for complete search history.

(56) References Cited

U.S. PATENT DOCUMENTS

| | | |
|---|---|---|
| 4,111,995 A | 9/1978 | Nelson |
| 4,253,199 A | 3/1981 | Banko |
| 4,254,509 A | 3/1981 | Tennant |
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |
| 4,435,856 A | 3/1984 | L'Esperance |
| 4,466,705 A | 8/1984 | Michelson |
| 4,490,860 A | 1/1985 | Rainin |

(Continued)

FOREIGN PATENT DOCUMENTS

EP    0898972 A2    3/1999

(Continued)

OTHER PUBLICATIONS

Esch et el, U.S. Appl. No. 11/844,108 entitled "Accommodating Intraocular Lens System and Method" filed Mar. 23, 2007.*

(Continued)

*Primary Examiner* — Paul Prebilic
(74) *Attorney, Agent, or Firm* — Shay Glenn LLP

(57) ABSTRACT

A deformable intracapsular implant device for shaping an enucleated lens capsule sac for use in cataract procedures and refractive lensectomy procedures. In one embodiment, the intraocular implant devices rely on thin film shape memory alloys and combine with the post-phaco capsular sac to provide a biomimetic complex that can mimic the energy-absorbing and energy-releasing characteristics of a young accommodative lens capsule. In another embodiment, the capsular shaping body is combined with an adaptive optic. The peripheral capsular shaping body carries at least one fluid-filled interior chamber that communicates with a space in a adaptive optic portion that has a deformable lens surface. The flexing of the peripheral shaping body in response to zonular tensioning and de-tensioning provides an inventive adaptive optics mechanism wherein fluid media flows between the respective chambers "adapts" the optic to increase and decrease the power thereof. In one embodiment, the capsular shaping body carries a posterior negative power adaptive optic that can be altered in power during accommodation to cooperate with an independent drop-in exchangeable intraocular lens.

19 Claims, 31 Drawing Sheets

U.S. PATENT DOCUMENTS

| | | | |
|---|---|---|---|
| 4,494,254 A | 1/1985 | Lopez | |
| 4,512,040 A | 4/1985 | McClure | |
| 4,528,311 A | 7/1985 | Beard et al. | |
| 4,575,373 A | 3/1986 | Johnson | |
| 4,585,457 A | 4/1986 | Kalb | |
| 4,604,295 A | 8/1986 | Humphreys | |
| 4,615,701 A * | 10/1986 | Woods | |
| 4,620,954 A | 11/1986 | Singer et al. | |
| 4,685,921 A | 8/1987 | Peyman | |
| 4,685,922 A | 8/1987 | Peyman | |
| 4,693,717 A | 9/1987 | Michelson | |
| 4,720,286 A | 1/1988 | Bailey et al. | |
| 4,731,078 A | 3/1988 | Stoy et al. | |
| 4,731,079 A * | 3/1988 | Stoy | 623/6.58 |
| 4,731,080 A | 3/1988 | Galin | |
| 4,784,485 A | 11/1988 | Ho | |
| 4,787,903 A | 11/1988 | Grendahl | |
| 4,790,847 A | 12/1988 | Woods | |
| 4,813,956 A | 3/1989 | Gupta | |
| 4,816,031 A | 3/1989 | Pfoff | |
| 4,836,201 A | 6/1989 | Patton et al. | |
| 4,842,601 A | 6/1989 | Smith | |
| 4,848,343 A | 7/1989 | Wallsten et al. | |
| 4,888,012 A | 12/1989 | Horn et al. | |
| 4,892,543 A | 1/1990 | Turley | |
| 4,902,293 A | 2/1990 | Feaster | |
| 4,919,151 A | 4/1990 | Grubbs et al. | |
| 4,932,966 A * | 6/1990 | Christie | |
| 4,946,469 A | 8/1990 | Sarafarazi | |
| 4,950,289 A | 8/1990 | Krasner | |
| 4,963,148 A | 10/1990 | Sulc et al. | |
| 4,994,082 A | 2/1991 | Richards et al. | |
| 4,995,879 A | 2/1991 | Dougherty | |
| 4,995,880 A | 2/1991 | Galib | |
| 5,015,254 A | 5/1991 | Greite | |
| 5,035,710 A | 7/1991 | Nakada et al. | |
| 5,047,051 A | 9/1991 | Cumming | |
| 5,061,914 A | 10/1991 | Busch et al. | |
| 5,066,301 A | 11/1991 | Wiley | |
| 5,145,884 A | 9/1992 | Yamamoto et al. | |
| 5,145,935 A | 9/1992 | Hayashi | |
| 5,152,789 A | 10/1992 | Willis | |
| 5,171,266 A | 12/1992 | Wiley et al. | |
| 5,201,763 A | 4/1993 | Brady et al. | |
| 5,213,579 A | 5/1993 | Yamada et al. | |
| 5,224,957 A | 7/1993 | Gasser et al. | |
| 5,235,003 A | 8/1993 | Ward et al. | |
| 5,251,993 A | 10/1993 | Sigourney | |
| 5,275,623 A | 1/1994 | Sarfarazi | |
| 5,275,624 A | 1/1994 | Hara et al. | |
| 5,288,293 A | 2/1994 | O'Donnell, Jr. | |
| 5,290,892 A | 3/1994 | Namdaran et al. | |
| 5,326,347 A | 7/1994 | Cumming | |
| 5,405,386 A | 4/1995 | Rheinish et al. | |
| 5,443,506 A * | 8/1995 | Garabet | 623/6.13 |
| 5,444,106 A | 8/1995 | Zhou | |
| 5,476,514 A | 12/1995 | Cumming | |
| 5,489,302 A | 2/1996 | Skottun | |
| 5,496,366 A | 3/1996 | Cumming | |
| 5,506,300 A | 4/1996 | Ward et al. | |
| 5,512,609 A * | 4/1996 | Yang | 523/107 |
| 5,578,081 A | 11/1996 | McDonald | |
| 5,585,049 A | 12/1996 | Grisoni et al. | |
| 5,593,436 A | 1/1997 | Langerman | |
| 5,607,472 A * | 3/1997 | Thompson | |
| 5,628,795 A | 5/1997 | Langerman | |
| 5,665,822 A | 9/1997 | Bitler et al. | |
| 5,674,282 A | 10/1997 | Cumming | |
| 5,697,973 A | 12/1997 | Peyman et al. | |
| 5,702,441 A | 12/1997 | Zhou | |
| 5,774,273 A | 6/1998 | Bornhorst | |
| 5,776,191 A | 7/1998 | Mazzocco | |
| 5,776,192 A | 7/1998 | McDonald | |
| 5,843,188 A | 12/1998 | McDonald | |
| 5,891,931 A | 4/1999 | Leboeuf et al. | |
| 5,928,282 A | 7/1999 | Nigam | |
| 5,964,802 A | 10/1999 | Anello et al. | |
| 5,984,962 A | 11/1999 | Anello et al. | |
| 6,013,101 A | 1/2000 | Israel | |
| 6,015,842 A | 1/2000 | Leboeuf et al. | |
| 6,102,539 A | 8/2000 | Tucker | |
| 6,117,171 A | 9/2000 | Skottun | |
| 6,124,980 A | 9/2000 | Cerbell | |
| 6,139,576 A | 10/2000 | Doyle et al. | |
| 6,160,084 A | 12/2000 | Langer et al. | |
| 6,176,878 B1 | 1/2001 | Qwon et al. | |
| 6,180,687 B1 | 1/2001 | Hammer et al. | |
| 6,188,526 B1 | 2/2001 | Sasaya et al. | |
| 6,190,410 B1 | 2/2001 | Lamielle et al. | |
| 6,195,807 B1 | 3/2001 | Chou | |
| 6,197,059 B1 | 3/2001 | Cumming | |
| 6,217,612 B1 * | 4/2001 | Woods | 623/6.37 |
| 6,225,367 B1 | 5/2001 | Chaouk et al. | |
| 6,229,641 B1 * | 5/2001 | Kosaka | 359/337 |
| 6,299,641 B1 * | 10/2001 | Woods | |
| 6,302,911 B1 * | 10/2001 | Hanna | |
| 6,322,589 B1 * | 11/2001 | Cumming | |
| 6,342,073 B1 * | 1/2002 | Cumming | |
| 6,387,126 B1 | 5/2002 | Cumming | |
| 6,388,043 B1 | 5/2002 | Langer et al. | |
| 6,406,494 B1 * | 6/2002 | Laguette et al. | 623/6.37 |
| 6,413,262 B2 | 7/2002 | Saishin et al. | |
| 6,423,094 B1 | 7/2002 | Sarfarazi | |
| 6,443,985 B1 * | 9/2002 | Woods | 623/6.46 |
| 6,450,642 B1 | 9/2002 | Jethmalani et al. | |
| 6,464,725 B2 | 10/2002 | Skottun | |
| 6,488,708 B2 * | 12/2002 | Sarfarazi | 623/6.34 |
| 6,493,151 B2 | 12/2002 | Schachar | |
| 6,494,911 B2 | 12/2002 | Cumming | |
| 6,503,276 B2 * | 1/2003 | Lang et al. | 623/6.37 |
| 6,517,577 B1 | 2/2003 | Callahan et al. | |
| 6,551,354 B1 * | 4/2003 | Ghazizadeh et al. | 623/6.43 |
| 6,552,860 B1 | 4/2003 | Alden | |
| 6,554,859 B1 * | 4/2003 | Lang et al. | 623/6.28 |
| 6,585,768 B2 | 7/2003 | Hamano et al. | |
| 6,589,550 B1 | 7/2003 | Hodd et al. | |
| 6,592,621 B1 | 7/2003 | Domino | |
| 6,599,317 B1 | 7/2003 | Weinschenk et al. | |
| 6,601,956 B1 | 8/2003 | Jean et al. | |
| 6,610,350 B2 | 8/2003 | Suzuki et al. | |
| 6,616,692 B1 | 9/2003 | Glick et al. | |
| 6,638,304 B2 | 10/2003 | Azar | |
| 6,638,305 B2 * | 10/2003 | Laguette | 623/6.37 |
| 6,638,306 B2 | 10/2003 | Cumming | |
| 6,645,245 B1 | 11/2003 | Preussner | |
| 6,645,246 B1 * | 11/2003 | Weinschenk et al. | 623/6.37 |
| 6,656,223 B2 | 12/2003 | Brady | |
| 6,660,035 B1 * | 12/2003 | Lang et al. | 623/6.37 |
| 6,692,525 B2 | 2/2004 | Brady et al. | |
| 6,695,881 B2 * | 2/2004 | Peng et al. | 623/6.34 |
| 6,709,108 B2 | 3/2004 | Levine et al. | |
| 6,712,848 B1 | 3/2004 | Wolf et al. | |
| 6,730,123 B1 | 5/2004 | Klopotek | |
| 6,743,388 B2 | 6/2004 | Sridharan et al. | |
| 6,749,632 B2 | 6/2004 | Sandstedt et al. | |
| 6,749,634 B2 | 6/2004 | Hanna | |
| 6,786,934 B2 | 9/2004 | Zadno-Azizi et al. | |
| 6,818,158 B2 | 11/2004 | Pham et al. | |
| 6,827,738 B2 | 12/2004 | Willis et al. | |
| 6,836,374 B2 | 12/2004 | Esch et al. | |
| 6,860,601 B2 | 3/2005 | Shadduck | |
| 6,878,320 B1 | 4/2005 | Alderson et al. | |
| 6,884,261 B2 | 4/2005 | Zadno-Azizi et al. | |
| 6,899,732 B2 | 5/2005 | Zadno-Azizi et al. | |
| 6,899,850 B2 | 5/2005 | Haywood et al. | |
| 6,926,736 B2 * | 8/2005 | Peng et al. | 623/6.34 |
| 6,935,743 B2 | 8/2005 | Shadduck | |
| 6,966,649 B2 * | 11/2005 | Shadduck | 351/177 |
| 6,969,403 B2 * | 11/2005 | Peng et al. | 623/6.34 |
| 7,060,094 B2 * | 6/2006 | Shahinpoor et al. | 623/4.1 |
| 7,068,439 B2 | 6/2006 | Esch | |
| 7,122,053 B2 | 10/2006 | Esch | |
| 7,217,288 B2 | 5/2007 | Esch et al. | |
| 7,247,168 B2 * | 7/2007 | Esch et al. | 623/6.37 |
| 7,264,351 B2 | 9/2007 | Shadduck | |
| 7,276,619 B2 | 10/2007 | Kunzler et al. | |
| 7,278,739 B2 | 10/2007 | Shadduck | |

| | | | |
|---|---|---|---|
| 7,494,505 B2 | 2/2009 | Kappelhof et al. | |
| 7,763,069 B2 | 7/2010 | Brady et al. | |
| 2001/0001836 A1 | 5/2001 | Cumming | |
| 2001/0016771 A1 | 8/2001 | Cumming | |
| 2001/0039449 A1* | 11/2001 | Johnson et al. | 623/1.19 |
| 2002/0002404 A1 | 1/2002 | Sarfarazi | |
| 2002/0046783 A1* | 4/2002 | Johnson et al. | 148/219 |
| 2002/0055777 A1 | 5/2002 | Cumming et al. | |
| 2002/0068971 A1 | 6/2002 | Cumming | |
| 2002/0072795 A1 | 6/2002 | Green | |
| 2002/0095212 A1 | 7/2002 | Boehm | |
| 2002/0107568 A1 | 8/2002 | Zadno-Azizi et al. | |
| 2002/0111678 A1 | 8/2002 | Zadno-Azizi et al. | |
| 2002/0116057 A1 | 8/2002 | Ting et al. | |
| 2002/0116058 A1 | 8/2002 | Zadno-Azizi et al. | |
| 2002/0116059 A1 | 8/2002 | Zadno-Azizi et al. | |
| 2002/0116060 A1 | 8/2002 | Nguyen et al. | |
| 2002/0116061 A1 | 8/2002 | Zadno-Azizi et al. | |
| 2002/0133228 A1 | 9/2002 | Sarver | |
| 2002/0143395 A1 | 10/2002 | Skottun | |
| 2002/0161434 A1 | 10/2002 | Laguette et al. | |
| 2002/0161435 A1 | 10/2002 | Portney | |
| 2002/0177896 A1* | 11/2002 | Israel | 623/6.37 |
| 2002/0193876 A1 | 12/2002 | Lang et al. | |
| 2003/0003295 A1 | 1/2003 | Dreher et al. | |
| 2003/0004569 A1 | 1/2003 | Haefliger | |
| 2003/0018384 A1 | 1/2003 | Valyunin et al. | |
| 2003/0042176 A1 | 3/2003 | Alderson et al. | |
| 2003/0050695 A1 | 3/2003 | Lin et al. | |
| 2003/0050696 A1 | 3/2003 | Cumming | |
| 2003/0060878 A1 | 3/2003 | Shadduck | |
| 2003/0060881 A1 | 3/2003 | Glick et al. | |
| 2003/0078656 A1 | 4/2003 | Nguyen | |
| 2003/0078657 A1 | 4/2003 | Zadno-Azizi et al. | |
| 2003/0078658 A1 | 4/2003 | Zadno-Azizi | |
| 2003/0083744 A1 | 5/2003 | Khoury | |
| 2003/0109925 A1 | 6/2003 | Ghazizadeh et al. | |
| 2003/0109926 A1 | 6/2003 | Portney | |
| 2003/0130732 A1 | 7/2003 | Sarfarazi | |
| 2003/0135272 A1 | 7/2003 | Brady et al. | |
| 2003/0149480 A1 | 8/2003 | Shadduck | |
| 2003/0158599 A1 | 8/2003 | Brady et al. | |
| 2003/0171808 A1 | 9/2003 | Phillips | |
| 2003/0183960 A1 | 10/2003 | Buazza et al. | |
| 2003/0187505 A1 | 10/2003 | Liao | |
| 2003/0199977 A1 | 10/2003 | Cumming | |
| 2003/0204254 A1 | 10/2003 | Peng et al. | |
| 2003/0204255 A1 | 10/2003 | Peng et al. | |
| 2003/0204256 A1 | 10/2003 | Peng et al. | |
| 2004/0008419 A1 | 1/2004 | Schachar | |
| 2004/0015236 A1 | 1/2004 | Sarfarazi | |
| 2004/0082993 A1 | 4/2004 | Woods | |
| 2004/0082994 A1* | 4/2004 | Woods et al. | 623/6.34 |
| 2004/0088050 A1 | 5/2004 | Norrby et al. | |
| 2004/0111153 A1* | 6/2004 | Woods et al. | 623/6.37 |
| 2004/0127984 A1 | 7/2004 | Paul et al. | |
| 2004/0169932 A1* | 9/2004 | Esch et al. | 359/665 |
| 2004/0181279 A1 | 9/2004 | Nun | |
| 2004/0190153 A1 | 9/2004 | Esch | |
| 2004/0230203 A1 | 11/2004 | Yaguchi | |
| 2005/0021139 A1 | 1/2005 | Shadduck | |
| 2005/0119740 A1 | 6/2005 | Esch et al. | |
| 2005/0131535 A1* | 6/2005 | Woods | 623/6.37 |
| 2005/0149183 A1 | 7/2005 | Shadduck | |
| 2005/0165410 A1 | 7/2005 | Zadno-Azizi et al. | |
| 2005/0251253 A1* | 11/2005 | Gross | 623/6.13 |
| 2005/0264756 A1 | 12/2005 | Esch | |
| 2006/0041307 A1 | 2/2006 | Esch et al. | |
| 2006/0069433 A1 | 3/2006 | Nun | |
| 2007/0010880 A1 | 1/2007 | Esch | |
| 2007/0088433 A1 | 4/2007 | Esch et al. | |
| 2007/0100445 A1 | 5/2007 | Shadduck | |
| 2007/0106377 A1 | 5/2007 | Smith et al. | |
| 2007/0203578 A1 | 8/2007 | Scholl et al. | |
| 2007/0213817 A1 | 9/2007 | Esch et al. | |
| 2007/0299487 A1 | 12/2007 | Shadduck | |
| 2008/0015689 A1 | 1/2008 | Esch et al. | |
| 2008/0200982 A1 | 8/2008 | Your | |
| 2010/0228344 A1* | 9/2010 | Shadduck | 623/6.18 |
| 2010/0228346 A1* | 9/2010 | Esch | 623/6.37 |

FOREIGN PATENT DOCUMENTS

| | | |
|---|---|---|
| FR | 2784575 | 4/2000 |
| JP | 07-044938 | 5/1995 |
| JP | 9294754 | 11/1997 |
| JP | 10-206609 | 8/1998 |
| JP | 11276509 | 10/1999 |
| JP | 11276509 A * | 10/1999 |
| RU | 1810052 | 4/1993 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |

OTHER PUBLICATIONS

Smith et el, U.S. Appl. No. 11/844,087 entitled "Accommodating Intraocular Lens System Having Spherical Aberration Compensation and Method," filed Aug. 23, 2007.*

Machine translation of Japanese language patent JP-11276509.*

Wyant et al; "Basic Wavefront Aberration Theory for Optical Metrology," Applied Optics and Optical Engineering, vol. XI, 1992:1-13.

Your, Jingjong; U.S. Appl. No. 12/177,720 entitled "Lens material and methods of curing with UV light," filed Jul. 22, 2008.

Smiley et al.; U.S. Appl. No. 12/177,857 entitled "Accommodating intraocular lenses and methods of use," filed Jul. 22, 2008.

Smiley et al.; U.S. Appl. No. 12/178,304 entitled "Post-implant accommodating lens modification," filed Jul. 23, 2008.

Smiley et al.; U.S. Appl. No. 12/178,565 entitled "Lens delivery system," filed Jul. 23, 2008.

Choi et al.; U.S. Appl. No. 12/178,454 entitled "Systems and methods for testing intraocular lenses," filed Jul. 23, 2008.

Baughman et al., "Negative poisson's ratios for extreme states fo matter," Science, vol. 288, pp. 1028-2022, Jun. 16, 2000.

Gordon, "Applications of shape memory polyurethanes," Proceedings of the First Intl Conf. on Shape Memory and Superelastic Tech., Asilomar Conference Center, Pacific Grove, CA, USA, pp. 115-119, 1994.

Jeon et al., "Shape memory and nonstructure in poly(norbornyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Dramatically stiffer elastic composite materials due to negative stiffness phase?," Journal of the Mechanics and Physics of Solids, vol. 50, pp. 979-1009, 2002.

Lakes et al., "Extreme damping in composite materials with negative-stiffness inclusions," Nature, vol. 410, pp. 565-567, Mar. 29, 2001.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2899, Mar. 26, 2001.

Lakes, "Lateral deformations in extreme matter," Science, vol. 288, pp. 1976, Jun. 2000.

Lakes, "Negative poisson's ratio materials," Science, vol. 238, pp. 551, Oct. 23, 1987.

Lakes, "No contractile obligations," Nature, vol. 358, pp. 713-714, 1992.

Li et al., "Crystallinity and morphology of segmented polyurethanes with different soft-segment length," Journal of Applied Polymer Science, vol. 62, pp. 631-638, 1996.

Liu et al., "Thermomechanical characterization of a tailored series of shape memory polymers," Journal of Applied Medical Polymers, vol. 6, No. 2, 2002.

Mather et al., "Strain recovery in POSS hybrid thermoplastics," Polymer Preprints, vol. 41, No. 1, pp. 528-529, 2000.

Lakes et al., "Microbuckling instability in elastomeric cellular solids," J. Materials Science, vol. 28, pp. 4667-4672, 1993.

Takahashi et al., "Structure and properties of shape-memory polyurethane block copolymers," Journal of Applied Polymer Science, vol. 60, pp. 1061-1069, 1996.

Tobushi et al., "Thermomechanical properties of shape memory polymers of polyurethane series and their applications," Journal de Physique IV, Colloque C1, vol. 6, pp. 377-384, 1996.

Xu et al., "Basic negative poisson's ratio microstructures by soft lithography," Advanced Materials, vol. 11, No. 14, 1999, pp. 1186-1189, 1999.

Shadduck, John H.; U.S. Appl. No. 12/347,816 entitled "Intraocular lenses and business methods," filed Dec. 31, 2008.

Gruber et al.; Exhaustive soxhlet extraction for the complete removal of residual compounds . . . ; Journal of Biomedical Materials Research; vol. 53; No. 5; pp. 445-448; Mar. 2000.

Shadduck, John H.; U.S. Appl. No. 12/694,184 entitled "Intraocular Lenses and Business Methods," filed Jan. 26, 2010.

Argento et al.; U.S. Appl. No. 12/685,531 entitled "Intraocular Lenses and Methods of Accounting for Capsule Size Variability and Post-Implant Changes in the Eye," filed Jan. 11, 2010.

Lendlein et al., "Shape-memory polymers," Angew. Chem. Int. Ed.; vol. 41; pp. 2034-2057; 2002.

Shadduck, John H.; U.S. Appl. No. 12/852,733 entitled "Intraocular Lens System and Method for Power Adjustment," filed Aug. 9, 2010.

Esch et al.; U.S. Appl. No. 12/853,892 entitled "Accommodating Intraocular Lens Having Peripherally Actuated Deflectable Surface and Method," filed Aug. 10, 2010.

Hildebrand et al.; U.S. Appl. No. 12/872,314 entitled "Lens Capsule Size Estimation," filed Aug. 31, 2010.

Conlisk, A. T. et al; Mass Transfer and Flow in Electrically Charged Micro- and Nano-channels; Analytical Chemistry, vol. 74; iss. 9; pp. 2139-2150; 2002.

Dubbelman et al.; The Thickness of the Aging Human Lens Obtained from Corrected Scheimpflug Images; Optometry & Vison Science; vo. 78; iss. 6; pp. 411-416; Jun. 2001.

Vass et al.; Prediction of pseudophakic capsular bag diameter based on biometric variables; J Cataract Refract Surg.; vol. 25; pp. 1376-1381; 1999.

Anvar et al.; U.S. Appl. No. 13/033,474 entitled "Fluid for Accommodating Intraocular Lenses," filed Feb. 23, 2011.

Gorder, P. F.; Electricity can pump medicine in implanted medical devices; Ohio State Research News; 3 pgs.; May 2, 2002 (printed from Internet Aug. 19, 2010).

Lendlein et al., "Biodegradable, elastic shape-memory polymers for potential biomedical applications", Science; vol. 296; pp. 1673-1676; May 31, 2002.

Metcalfe et al., "Cold hibernated elastic memory foams for endovascular interventions," Biomaterials, vol. 24, pp. 491-497, 2003.

\* cited by examiner lax zonules ZL:

tensioned zonules ZL

INTRAOCULAR IMPLANT DEVICES

CROSS-REFERENCE TO RELATED APPLICATIONS

This application claims benefit under 35 U.S.C. §119(e) of Provisional U.S. Patent Application Ser. No. 60/353,847 filed Feb. 2, 2002 titled Intraocular Lens and Method of Making. This application also claims benefit of the following other Provisional U.S. Patent Applications: Ser. No. 60/362,303 filed Mar. 6, 2002 titled Intraocular Lens and Method of Making; Ser. No. 60/378,600 filed May 7, 2002 titled Intraocular Devices and Methods of Making; Ser. No. 60/405,471 filed Aug. 23, 2002 titled Intraocular Implant Devices and Methods of Making, Ser. No. 60/408,019 filed Sep. 3, 2002 titled Intraocular Lens and Ser No. 60/431,110 filed Dec. 4, 2002 titled Intraocular Implant Devices and Methods of Making. All of the above applications are incorporated herein in their entirety by this reference.

BACKGROUND OF THE INVENTION

1. Field of the Invention

The present invention is directed to intraocular implant devices and more specifically to shape memory capsular shaping devices for combining with a post-phacoemulsification capsular sac to provide a biomimetic complex that can mimic the energy-absorbing and energy-releasing characteristics of a natural young accommodative lens capsule. The shape memory capsular shaping devices can further be combined with an independent or integrated optics to provide an accommodating intraocular lens.

2. Description of the Related Art

The human lens capsule can be afflicted with several disorders that degrade its functioning in the vision system. The most common lens disorder is a cataract which consists of the opacification of the normally clear, natural crystalline lens matrix in a human eye. The opacification usually results from the aging process but can also be caused by heredity or diabetes. FIG. 1A illustrates a lens capsule comprising a capsular sac with an opacified crystalline lens nucleus. In a typical cataract procedure as performed today, the patient's opaque crystalline lens is replaced with a clear lens implant or IOL. (See FIGS. 1A and 1B). The vast majority of cataract patients must wear prescription eyeglasses following surgery to see properly. The IOLs in use today provide the eye with a fixed focal length, wherein focusing on both close-up objects and distant objects is not possible. Intraocular lens implantation for cataracts is the most commonly performed surgical procedure in elderly patients in the U.S. Nearly three million cataract surgeries are performed each year in the U.S., with an additional 2.5 million surgeries in Europe and Asia.

Mechanisms of Accommodation. Referring to FIG. 1A, the human eye defines an anterior chamber 10 between the cornea 12 and iris 14 and a posterior chamber 20 between the iris and the lens capsule 102. The vitreous chamber 30 lies behind the lens capsule. The lens capsule 102 that contains the crystalline lens matrix LM or nucleus has an equator that is attached to cobweb-like zonular ligaments ZL that extend generally radially outward to the ciliary muscle attachments. The lens capsule 102 has transparent flexible anterior and posterior walls or capsular membranes that contain the crystalline lens matrix LM.

Accommodation occurs when the ciliary muscle CM contracts to thereby release the resting zonular tension on the equatorial region of the lens capsule 102. The release of zonular tension allows the inherent elasticity of the lens capsule to alter it to a more globular or spherical shape, with increased surface curvatures of both the anterior and posterior lenticular surfaces. The lens capsule together with the crystalline lens matrix and its internal pressure provides the lens with a resilient shape that is more spherical in an untensioned state. Ultrasound biomicroscopic (UBM) images also show that the apex of the ciliary muscle moves anteriorly and inward—at the same time that the equatorial edge the lens capsule moves inwardly from the sclera during accommodation.

When the ciliary muscle is relaxed, the muscle in combination with the elasticity of the choroid and posterior zonular fibers moves the ciliary muscle into the unaccommodated configuration, which is posterior and radially outward from the accommodated configuration. The radial outward movement of the ciliary muscles creates zonular tension on the lens capsule to stretch the equatorial region of lens toward the sclera. The disaccommodation mechanism flattens the lens and reduces the lens curvature (both anterior and posterior). Such natural accommodative capability thus involves contraction and relaxation of the ciliary muscles by the brain to alter the shape of the lens to the appropriate refractive parameters for focusing the light rays entering the eye on the retina—to provide both near vision and distant vision.

In conventional cataract surgery as depicted in FIGS. 1B and 1C, the crystalline lens matrix is removed leaving intact only the thin walls of the anterior and posterior capsules—together with zonular ligament connections to the ciliary muscles. The crystalline lens core is removed by phacoemulsification through a curvilinear capsularrhexis as illustrated in FIG. 1B, i.e., the removal of an anterior portion of the capsular sac. FIG. 1B then depicts a conventional 3-piece IOL just after implantation in the capsular sac.

FIG. 1C next illustrates the capsular sac and the prior art 3-piece IOL after a healing period of a few days to weeks. It can be seen that the capsular sac effectively shrink-wraps around the IOL due to the capsularrhexis, the collapse of the walls of the sac and subsequent fibrosis. As can be easily understood from FIGS. 1B and 1C, cataract surgery as practiced today causes the irretrievable loss of most of the eye's natural structures that provide accommodation. The crystalline lens matrix is completely lost—and the integrity of the capsular sac is reduced by the capsularrhexis. The shrink-wrap of the capsular sac around the IOL damages the zonule complex, and thereafter it is believed that the ciliary muscles will atrophy.

Prior Art Pseudo-Accommodative Lens Devices. At least one commercially available IOL, and others in clinical trials, are claimed to "accommodate" even though the capsular sac shrink-wraps around the IOL as shown in FIG. 1C. If any such prior art lens provide variable focusing power, it is better described as pseudo-accommodation since all the eye's natural accommodation mechanisms of changing the shape of the lens capsule are not functioning. Perhaps the most widely known of the pseudo-accommodative IOLs is a design patented by Cumming which is described in patent disclosures as having hinged haptics that are claimed to flex even after the capsular sac is shrink-wrapped around the haptics. Cumming's patents (e.g., U.S. Pat. Nos. 5,496,366; 5,674,282; 6,197,059; 6,322,589; 6,342,073; 6,387,126) describe the hinged haptics as allowing the lens element to be translated forward and backward in response to ciliary muscle contraction and relaxation within the shrink-wrapped capsule. The Cumming IOL design is being commercialized by C&C Vision, 6 Journey, Ste. 270, Aliso Viejo, Calif. 92656 as the CrystaLens AT-45. However, the medical monitor for the CrystaLens AT-45 in Phase I FDA trials explained in an American Society of Cataract and Refractive Surgeons (AS-CRS) presentation, when asked about movement of AT-45's hinged haptics, that the AT-45 was not "moving much" at the optic and hinge. It is accepted that the movement of such a lens is entirely pseudoaccommodative and depends on vitreous displacement that pushes the entire IOL slightly anteriorly (see: http://www.candcvision.com/ASCRSCCTalks/Slade/Slade.htm). A similar IOL that is implanted in a shrink-wrapped capsule and in sold in Europe by HumanOptics, Spardorfer Strasse 150, 90154 Erlangen, Germany. The HumanOptics lens is the Akkommodative 1CU which is not available in the U.S., due to lack of FDA approval. In sum, any prior art IOLs that are implanted in an enucleated, shrink-wrapped lens capsule probably are not flexed by ciliary muscle relaxation, and exhibit only a pseudo-accommodative response due to vitreous displacement.

Since surgeons began using IOLs widely in the 1970's, IOL design and surgical techniques for IOL implantation have undergone a continuous evolution. While less invasive techniques for IOL implantation and new IOL materials technologies have evolved rapidly in the several years, there has been no real development of technologies for combining the capsular sac with biocompatible materials to provide a biomimetic capsular complex. What has stalled all innovations in designing a truly resilient (variable-focus) post-phaco lens capsule has been is the lack of sophisticated materials.

What has been needed are materials and intraocular devices that be introduced into an enucleated lens capsule with a 1 mm. to 2.5 mm. injector, wherein the deployed device and material provide the exact strain-absorbing properties and strain-releasing properties needed to cooperate with natural zonular tensioning forces. Such an intraocular device will allow for the design of dynamic IOLs that can replicate natural accommodation. Microdevices of intelligent elastic composite materials can provide the enabling technology to develop new classes of accommodating IOL systems.

SUMMARY OF THE INVENTION

This invention relates to novel shape memory devices, materials and capsular shaping elements (CSEs) that can be implanted using conventional techniques to create a biomimetic lens capsule complex. The capsular shaping element, or more specifically an intracapsular implant, is designed to provide the implant/lens capsule complex with a shape and resiliency that mimics the elasticity of a young, still-accommodative lens capsule. In one embodiment, the capsular shaping element incorporates at least one thin-film expanse of a shape memory alloy (SMA) material in a three dimensional shape to impart the required elasticity to the CSE. The capsular shaping element will enable, and can be integrated with, several classes of optic elements to provide an accommodative IOL system that cooperates with ciliary muscle tensioning and de-tensioning to provide variable focusing power. The accommodating IOL corresponding to the invention can be used following typical cataract surgeries, or can be used in refractive lensectomy procedures to treat presbyopia.

In a preferred embodiment, the capsular shaping element incorporates a least one formed expanse of thin-film nickel titanium alloy (NiTi or Nitinol). Nitinol materials have the unique capability to absorb energy by a reversible crystalline transformation (superelasticity) which is orders of magnitude higher than can be absorbed in plastic deformations of conventional resilient materials, such as a polymers used in other so-called accommodating IOL designs. In addition, such NiTi materials have the ability to avoid localization of plastic deformations—and thus can spread the absorbed energy over a much larger region of the material. Further, a capsular shaping element that relies on NiTi for its shape memory characteristics need only be microns in thickness for compacted introduction into the lens capsule. The implant, in fact, may be little thicker than the lens capsule itself. Nickel titanium alloys are also known to be biocompatible. In preferred variants of biomimetic CSEs described herein, the implant carries at least one seamless expanse of thin-film NiTi material that three dimensionally formed to engage the anterior and posterior capsules—while leaving an open central optic zone. Various types of optic elements can be coupled to the capsular shaping element of the invention.

In such preferred embodiments, the capsular shaping body also comprises in part a shape memory polymer (SMP) component that encases the shape memory alloy form, whether of a thin film SMA or another formed structure of a nickel titanium alloy. The shape memory polymer is capable of a memory shape as well as a compacted temporary shape. In its temporary compacted shape, the polymer together with the embedded superelastic nickel titanium can be ultrathin and three dimensionally stable to be rollable for use in standard diameter injector or even a sub-1 mm. injector.

In another preferred embodiment, the non-optic or peripheral body portion of the implant is again of a shape memory polymer, and optional SMA form, that engages the enucleated lens capsule to provide a post-phaco biomimetic complex that mimics the energy-absorbing and energy-releasing characteristics of an accommodative lens capsule. An adaptive lens element is coupled to the annular peripheral body portion. In this embodiment, the peripheral capsular shaping portion of the implant body carries at least one fluid-filled interior chamber that communicates with a central chamber in the adaptive lens element that actuates a deformable surface thereof. The flexing of the peripheral body portion in response to zonular tensioning and de-tensioning provides an adaptive optic mechanism wherein fluid media flows between the respective chambers to deform the lens surface to increase or decrease lens power. For example, in one embodiment, the peripheral body portion carries a posterior negative power lens that can be altered in power during accommodation to cooperate with a second lens element to provide variable focus.

Accordingly, a principal advantage of the present invention is the provision of deformable, rollable intraocular devices such as capsular shaping devices that utilize shape memory alloy forms, such shaping devices enabling an artificial lens system to provide accommodative amplitude (diopters of power modification).

The invention advantageously provides a capsular shaping element with integrated optics that require only a very small entry incision for implantation—for example a sub-1 mm. minimal incision through the cornea.

The invention advantageously provides an independent module comprising a capsular shaping structure of a thin film material that conforms to and maintains an intracapsular volume for receiving an IOL.

The invention provides a capsular shaping structure of a superelastic shape memory alloy form within a a shape memory polymer envelope that conforms to and maintains an intracapsular volume.

The invention advantageously provides an independent module comprising a capsular shaping structure that can cooperate with drop-in fixed focus IOL or a drop-in accommodating IOL.

The invention advantageously provides an independent module comprising a capsular shaping element that allows for simplified lens exchange.

The invention provides an independent module comprising a capsular shaping structure that is adapted to cooperate with, and amplify, zonular tensioning and de-tensioning caused by ciliary muscle relaxation and contraction to enable various types of an accommodating lens systems.

The invention advantageously provides a modular capsular shaping element that is adapted to cooperate with both (i) vitreous displacement caused by ciliary muscle contraction; and (ii) zonular tensioning and de-tensioning caused by ciliary muscle relaxation and contraction, to amplify lens translation in a novel types of accommodating lens systems.

The invention provides an IOL with optic or non-optic body portions that carry a photomodifiable SMP that can be irradiated to adjust an operational parameter of an adaptive optic or accommodating lens system.

The invention provides an IOL with a polymer non-optic body portion that carries an anti-fibrotic pharmacological agent for release about the capsular sac for preventing or limiting fibrosis and shrinkage of the capsular sac.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE PREFERRED EMBODIMENTS

I. Principles of Superelasticity and Shape Memory in Classes of Ophthalmic Implant Materials The capsular shaping element (CSE) of the invention is adapted for providing a biomimetic lens capsule complex that will enable an accommodative lens system, which can have several variants. The term biomimetic lens capsule is derived from the word biomimesis, which defines the development of structures that mimic life, or that imitate biological systems. In this case, the objective is to develop an implant that mimics the inherent elasticity of a young lens capsule for cooperating with the ciliary muscle to alter the shape or translation of an implanted optic element.

The biomimetic lens capsules corresponding to the invention are enabled by the phenomena of shape memory and superelasticity that are unique to certain newly developed so-called intelligent materials. In particular, one embodiment of CSE comprises a thin-film expanse of a nickel titanium alloy that is fabricated in a vacuum chamber deposition process. The nickel titanium form is embedded within a thin biocompatible polymer envelope. In the prior art, the principal uses of nickel titanium alloys have been developed from uniaxial models of superelasticity, such as in wires and other bulk materials. The invention extends the use of nickel titanium fabricated in thin film expanses. Additional embodiments comprise, at least in part, an expanse of a shape memory polymer (SMP), a shape memory polymer foam, or a bioerodible shape memory polymer.

Figure 1A:
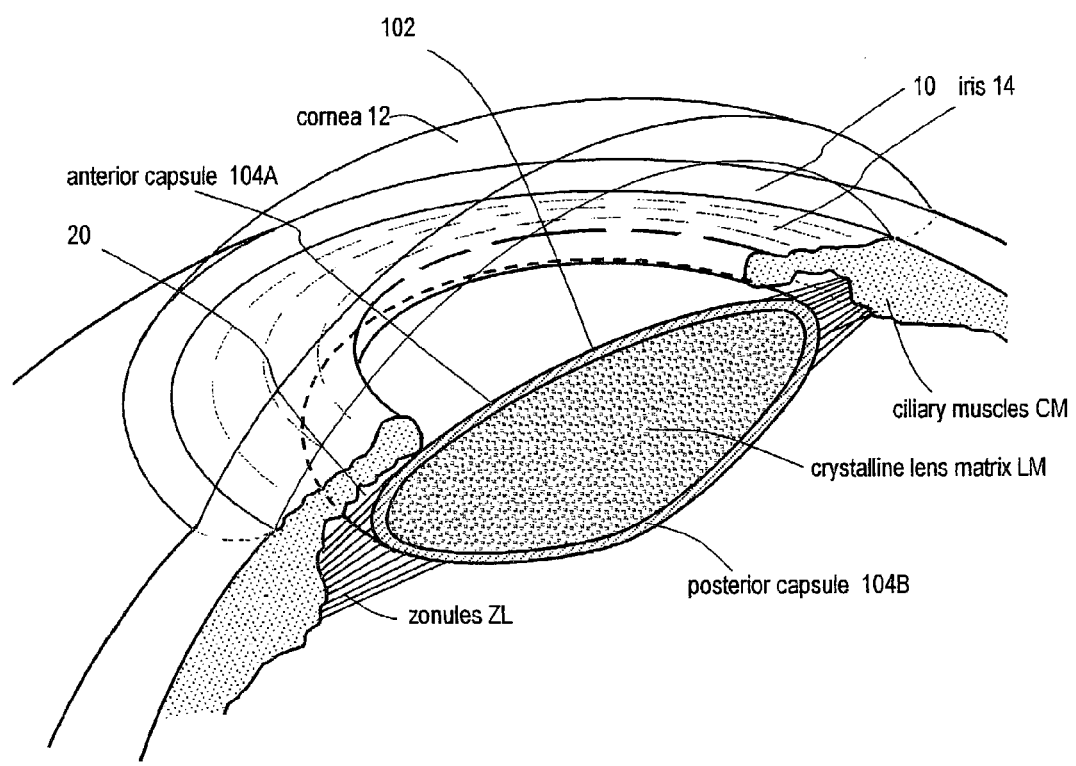
FIG. 1A is a perspective cut-away view of an eye with an opacified lens capsule.
Figure 1B:
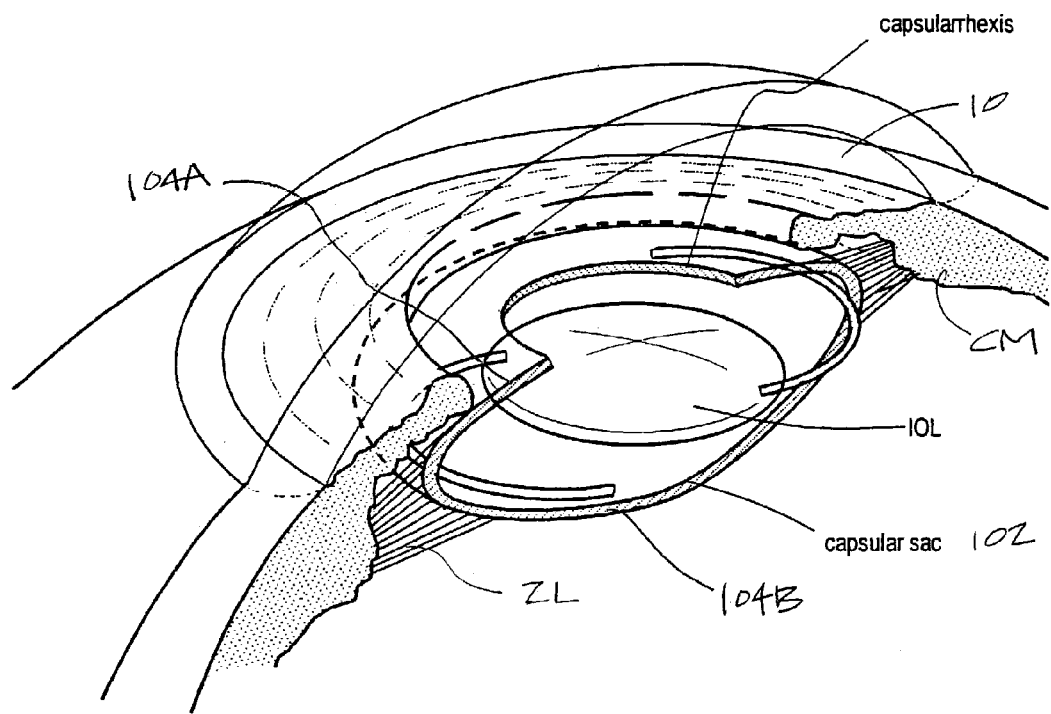
FIG. 1B is a perspective cut-away view of the eye of FIG. 1A with a curvilinear capsularrhexis and the crystalline lens matrix removed by phacoemulsification, together with the implantation of a prior art 3-piece IOL.
Figure 1C:
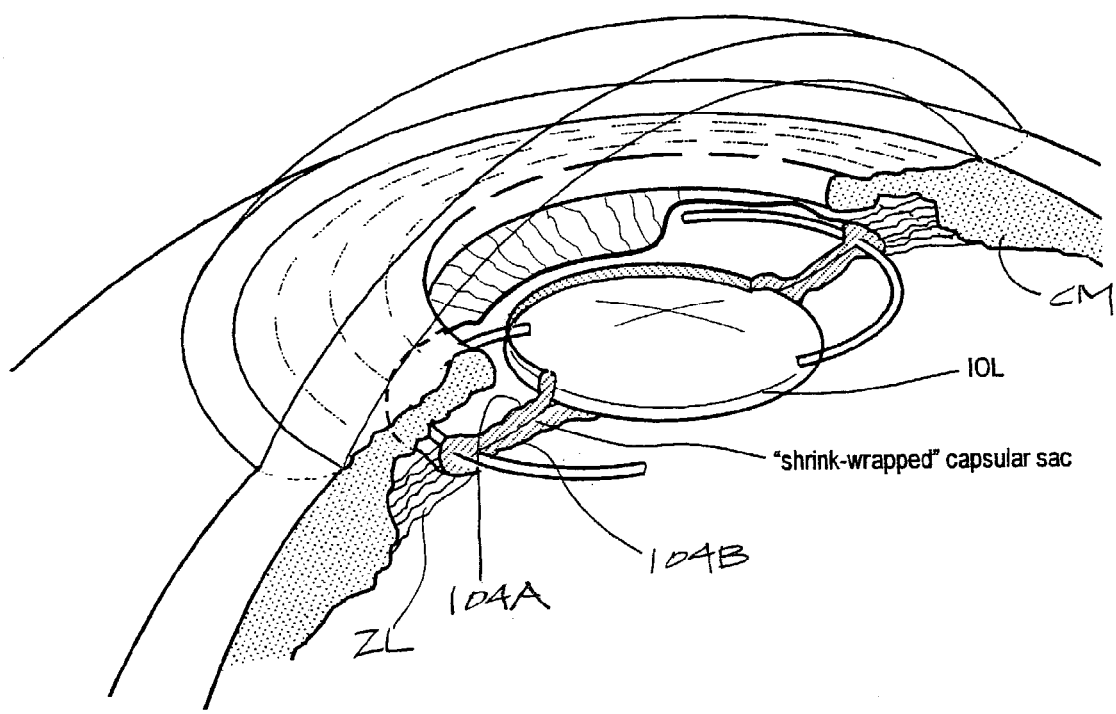
FIG. 1C is a perspective cut-away view of the eye of FIG. 1B showing the lens capsule after wound healing wherein the lens capsule shrink-wraps around the prior art IOL.
Figure 2:
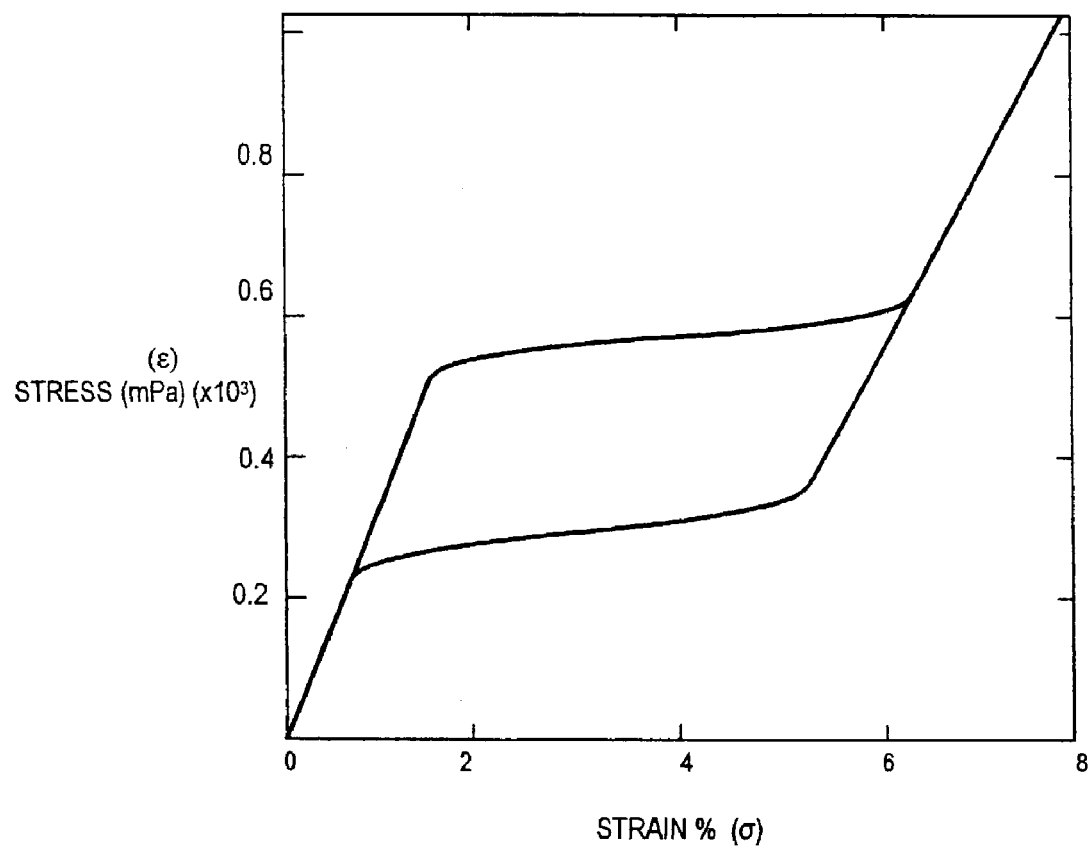
FIG. 2 is a stress-strain graph of the thin-film superelastic nickel titanium alloy that is utilized in a preferred embodiments of the invention.

In order to understand the invention, it is useful to describe the phenomena of shape memory and superelasticity that are unique to nickel titanium alloys, which are utilized in preferred embodiments of the capsular shaping structures of the invention. In an unstressed state, the nickel titanium alloy component will present itself in an austenite phase—in which phase it exhibits linear elasticity. When stress is applied to the material, the austenite phase transforms into a martensite phase that also exhibits linear elasticity, however, each phase has a different constant as can be seen in FIG. 2. The austhenite-martensite transformation produces a substantial level of strain ($\sigma$) that is developed over a relatively small range of stress ($\epsilon$). Upon unloading the stress, the transformation is reversible; however, the stress levels at which the reversible transformation occurs are smaller than the stresses that were require to produce the original austhenite-martensite transformation, as depicted in FIG. 2. Since, upon unloading, the material completely recovers it original shape, it is described as having elastic properties. In nickel titanium alloys, since the transformation strains are so large (greater that 6%) when compared to other alloys (typically on the order 0.1%), the material is defined as superelastic.

Figure 3A:
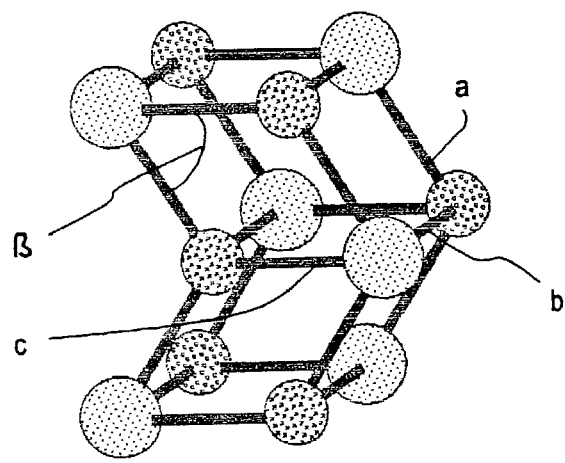
FIG. 3A is a schematic depiction of the crystalline lattice of the thin-film superelastic nickel titanium alloy of FIG. 2 in a martensite state.
Figure 3B:
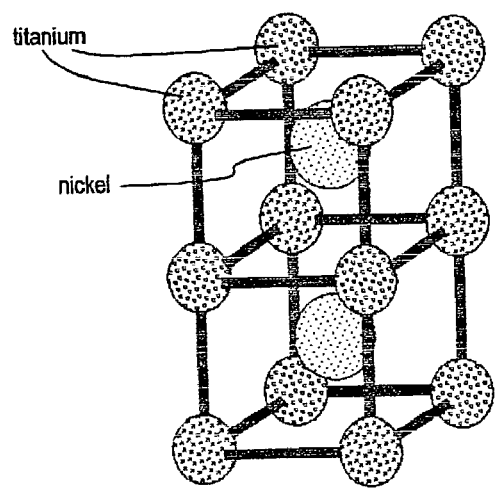
FIG. 3B is a depiction of the crystalline lattice of the superelastic nickel titanium alloy of FIG. 3A in its memory austhenite state.

The superelastic properties of NiTi, and its strain-induced martensite transformation, can be understood by schematic illustrations of its crystalline lattice structure. The austhentite and martensite phases each define a very distinct crystalline structure or phases, as depicted in FIGS. 3A and 3B. Which phase is present depends on temperature and the amount of stress (consider it as internal pressure) being applied to the material. If a thin-film expanse of nickel titanium alloy is cooled from above its transformation temperature, it will remain 100% austenite until it reaches the martensite start temperature $M_s$ for any particular amount of stress then being applied to the material. As depicted in FIG. 3A the sides of the martensite crystalline lattice marked a, b, and c are all different lengths. When pressure or stress (s) is applied to the lattice, these sides will change in length to compensate for the deformation forces. The angle marked $\beta$ also can change in response to such deforming forces. When the nickel titanium is elevated in temperature from below its crystallographic phase transition as shown in FIG. 3B, the material will recover its precise "memory" shape above its austenite start ($A_s$) temperature which can be designed to be slightly below body temperature (37° C.). In its austenite phase, the nickel titanium has only one possible crystalline orientation, which will be a pre-determined shape of the capsular shaping device. It is because of the wide variability of these lattice parameters that thin-film nickel titanium material can be easily deformed in its martensite phase. This accounts for the "rubbery" superelastic nature of NiTi that allows 6% or more recoverable elastic deformations.

The thin-film NiTi expanse of the invention can be fabricated as described in U.S. Pat. No. 5,061,914 to D. Busch and A. D. Johnson and the following published U.S. patent applications to A. D. Johnson et al.: No. 20020046783 A1 published Apr. 25, 2002; and No. 20010039449 A1 published Nov. 8, 2001. All of the patents and applications referred to in this paragraph are incorporated herein in their entirely by this reference.

The capsular shaping portion of the intracapsular implant corresponding to the invention also can be made in part, or in its entirety, from a class of shape memory polymer (SMP). The term "shape memory" is used in a different context when referring to SMPs. A shape memory polymer is said to demonstrate shape memory phenomena when it has a fixed temporary shape that can revert to a memory shape upon a selected stimulus, such as temperature. A shape memory polymer generally is characterized as defining phases that result from glass transition temperatures in segregated linear block co-polymers: a hard segment and a soft segment. The hard segment of SMP typically is crystalline with a defined melting point, and the soft segment is typically amorphous, with another defined transition temperature. In some embodiments, these characteristics may be reversed together with glass transition temperatures and melting points.

In one embodiment, when the SMP material is elevated in temperature above the melting point or glass transition temperature of the hard segment, the material then can be formed into a memory shape. The selected shape is memorized by cooling the SMP below the melting point or glass transition temperature of the hard segment. When the shaped SMP is cooled below the melting point or glass transition temperature of the soft segment while the shape is deformed, that (temporary) shape is fixed. The original shape is recovered by heating the material above the melting point or glass transition temperature of the soft segment but below the melting point or glass transition temperature of the hard segment. (Other methods for setting temporary and memory shapes are known which are described in the literature below). The recovery of the memory original shape is thus induced by an increase in temperature, and is termed the thermal shape memory effect of the polymer. The temperature can be at or below body temperature (37° C.) or a selected higher temperature.

Besides utilizing the thermal shape memory effect of the polymer, the memorized physical properties of the SMP can be controlled by its change in temperature or stress, particularly in ranges of the melting point or glass transition temperature of the soft segment of the polymer, e.g., the elastic modulus, hardness, flexibility, permeability and index of refraction. The scope of the invention of using SMPs in capsular shaping elements extends to the control of such physical properties, particularly in elastic composite structure described further below.

Examples of polymers that have been utilized in hard and soft segments of SMPs include polyurethanes, polynorborenes, styrene-butadiene co-polymers, cross-linked polyethylenes, cross-linked polycyclooctenes, polyethers, polyacrylates, polyamides, polysiloxanes, polyether amides, polyether esters, and urethane-butadiene co-polymers and others identified in the following patents and publications: U.S. Pat. No. 5,145,935 to Hayashi; U.S. Pat. No. 5,506,300 to Ward et al.; U.S. Pat. No. 5,665,822 to Bitler et al.; and U.S. Pat. No. 6,388,043 to Langer et al. (all of which are incorporated herein by reference); Mather, Strain Recovery in POSS Hybrid Thermoplastics, Polymer 2000, 41(1), 528; Mather et al., *Shape Memory and Nanostructure in Poly(Norbonyl-POSS) Copolymers*, Polym. Int. 49, 453-57 (2000); Lui et al., *Thermomechanical Characterization of a Tailored Series of Shape Memory Polymers*, J. App. Med. Plastics, Fall 2002; Gorden, *Applications of Shape Memory Polyurethanes*, Proceedings of the First International Conference on Shape Memory and Superelastic Technologies, SMST International Committee, pp. 115-19 (1994); Kim, et al., *Polyurethanes having shape memory effect*, Polymer 37(26):5781-93 (1996); Li et al., *Crystallinity and morphology of segmented polyurethanes with different soft-segment length*, J. Applied Polymer 62:631-38 (1996); Takahashi et al., *Structure and properties of shape-memory polyurethane block copolymers*, J. Applied Polymer Science 60:1061-69 (1996); Tobushi H., et al., *Thermomechanical properties of shape memory polymers of polyurethane series and their applications*, J. Physique IV (Colloque C1) 6:377-84 (1996)) (all of the cited literature incorporated herein by this reference).

The scope of the invention extends to the use of SMP foams for use in elastic composite structures, wherein the capsular shaping element utilizes the polymer foam together with an expanse of nickel titanium alloy. See Watt A. M., et al., *Thermomechanical Properties of a Shape Memory Polymer Foam*, available from Jet Propulsion Laboratories, 4800 Oak Grove Drive, Pasadena Calif. 91109 (incorporated herein by reference). SMP foams function in a similar manner as the shape memory polymers described above. The scope of the invention also extends to the use of shape memory polymers that are sometimes called two-way shape memory polymers that can moved between two predetermined memory shapes in response to varied stimuli, as described in U.S. Pat. No. 6,388,043 to Langer et al. (incorporated herein by reference).

Other derivatives of SMPs within the scope of the invention fall into the class of bioerodible shape memory polymers that again may be used in certain elastic composite capsular shaping structures. As will be described below, one embodiment of capsular shaping element may be designed with composite portions that define a first modulus of elasticity for a period of time after implantation to resist force that may be applied by fibrosis during wound healing, followed by a second modulus of elasticity following biodegradation of a surface portion of the elastic composite structure.

In all variants of capsular shaping element that make use of expanses of thin films or composites of shape memory materials, the principal objectives relate to the design of an implant that will impart to the implant/lens capsule complex an unstressed more spherical shape with a lesser equatorial diameter when zonular tension is relaxed, and a stressed flatter shape with a greater equatorial diameter in response to zonular tensioning forces. The superelastic component will provide the ability to absorb known amounts of stress—and release the energy in a predetermined manner in millions of cycles over the lifetime of the implant in cooperation with an optic that will provide variable focus.

Figure 4:
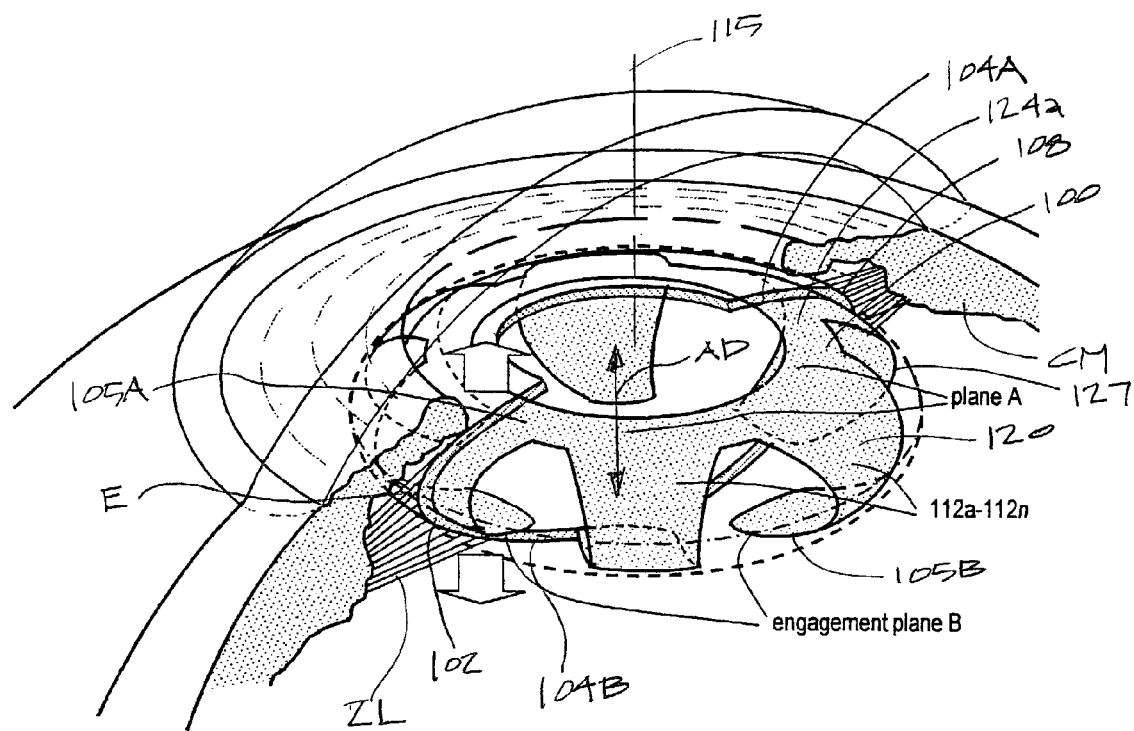
FIG. 4 is a perspective cut-away view of a lens capsule and Type "A" intraocular device corresponding to the invention comprising a deformable, rollable ultrathin capsular shaping clement (CSE) of a thin-film expanse of shape memory material encased in a polymer.
Figure 5:
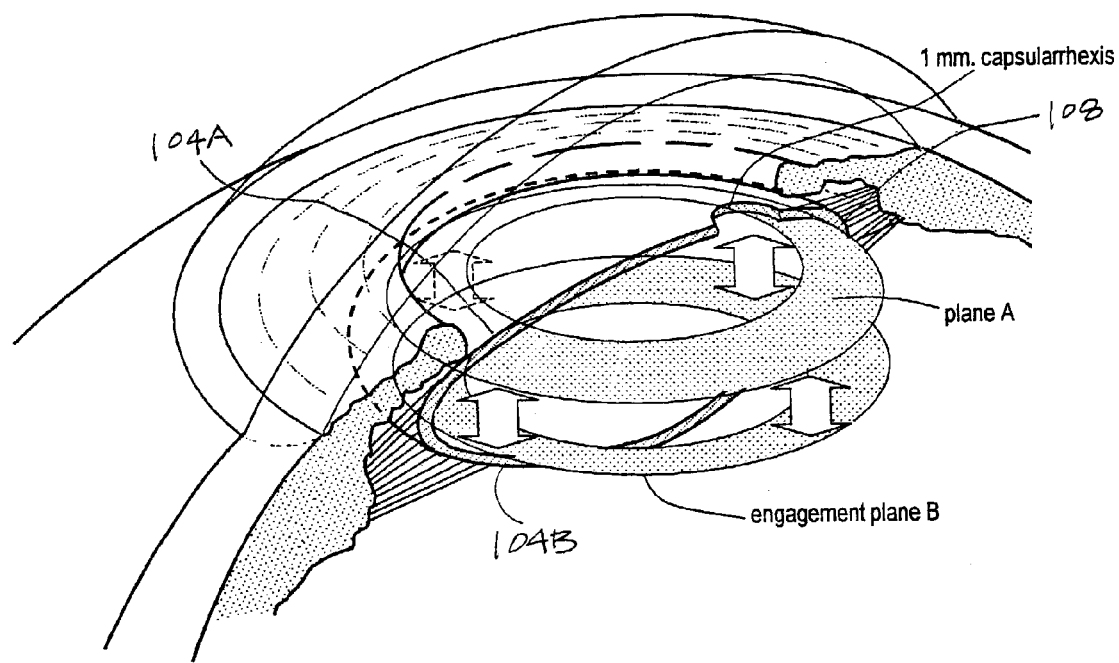
FIG. 5 is a perspective cut-away view of the lens capsule of FIG. 4 that illustrates anterior and posterior engagement planes of the capsule that targeted for engagement by the Type "A" capsular shaping element (CSE) of FIG. 4.

II. Exemplary Biomimetic Intracapsular Devices with Superelastic or Elastic Composite Components A. Type "A" Implantable Intraocular Devices. FIG. 4 illustrates a cut-away view of an ultrathin flexible, deformable intraocular device (IOD) in the form of a capsular shaping element 100 corresponding to the present invention implanted in a capsular sac or bag 102. FIG. 5 illustrates a hypothetical capsular sac 102 that defines an anterior capsule 104A and a posterior capsule 104B after removal of the crystalline lens matrix LM. This disclosure will adopt the terminology commonly used by ophthalmologists that defines the anterior capsule as the portion of the capsular sac anterior to the capsular equator 108, and the posterior capsule as the sac portion posterior to the equatorial region. In FIG. 5, it can be seen that an anterior engagement plane A and a posterior engagement plane B comprise annular (inner) portions of the anterior and posterior capsules 104A and 104B that are substantially engaged by the capsular shaping element 100 of FIG. 4. The anterior plane A and posterior plane B are radially outward of a central optic zone indicated at C that ranges from about 4.5 to 7.0 mm in diameter. The anterior and posterior planes A and B are radially inward of an equatorial region indicated at E. In this disclosure, the term axis and its reference numeral 115 are applied to both the natural lens capsule and the capsular shaping element 100, and the term axis generally describes the optical axis of the vision system. The axial dimension AD refers to the dimension of the capsular implant or implant/lens capsule complex along axis 115.

In FIG. 4, the capsular shaping element 100 comprises a thin-film expanse 120 of a shape memory material, in this case a nickel titanium alloy, that is encased in a thin layer or coating of a biocompatible polymer 122. FIG. 4 thus shows the capsular shaping element 100 in a perspective view as it would appear in an unstressed state—similar to its appearance prior to its implantation—and maintaining the lens capsule in an open more spherical shape. The combination of the capsular shaping element 100 and the natural lens capsule, defined herein as the implant/lens capsule complex, is adapted to provide a biomimetic lens capsule that can cooperate with the eye's natural accommodation mechanisms to enable a new class of accommodating lens systems that mimic a naturally accommodative human lens capsule.

The IOD 100 of FIG. 4 defines a first anterior surface portion 105A that is adapted to engage the anterior plane A of the anterior capsule 104A of FIG. 5. The capsular shaping element 100 further defines a second posterior surface portion 105B that is adapted to engage the posterior plane B of the posterior capsule 104B of FIG. 5. The capsular shaping element 100 of FIG. 4 illustrates a device that has a discrete number of spaced apart peripheral arcuate extending body portions 112a-112n (where n indicates an integer) that are formed to extend from the anterior plane A of anterior capsule 104A to posterior plane B of posterior capsule 104B in a meridonal manner relative to axis 115. In FIG. 4, the peripheral extending portions 112a-112n transition to an anterior annular body portion indicated at 124a. As will be described in another embodiment below, the annular body portion 124a can be positioned anteriorly or posteriorly in the capsular sac. In the embodiment of FIG. 4, the posterior surface portion 105B comprises a plurality of regions of each arcuate peripheral body portion 112a-112n. It should be appreciated that the number of spaced apart arcuate peripheral portions 112a-112n can range from about 2 to 20, and moreover the wall portion 127 of the capsular shaping element 100 further can extend about the entire circumference of the IOD so that there would not be a plurality of discrete elements, particularly when an elastic composite is used as will be described below.

Figure 6:
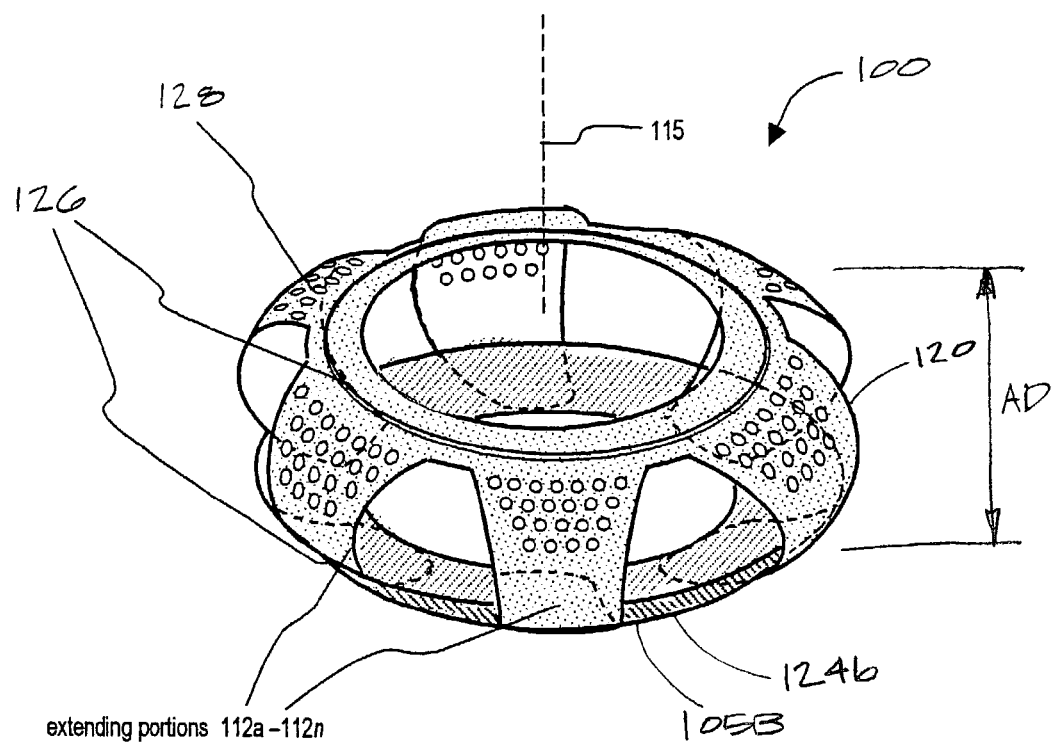
FIG. 6 is a cut-away view of an alternative Type "A" capsular shaping element similar to that of FIG. 4 with a posterior annular body portion of a polymer.

FIG. 6 shows an alternative embodiment wherein the capsular shaping structure 100 has other optional features and characteristics. First, the thin-film shape memory expanse 120 is insert-molded with a foldable posterior annular polymer portion 124b to thereby provide a broader posterior surface portion 105B to engage plane B of the capsular sac. Further, the intracapsular implant defines an at least partly annular abrupt edge portion 126 (collectively) or projecting ridge for engaging the capsule interior to limit cell migration within the interface between the lens capsule and the implant. Preferably, such an annular edge 126 is provided both on the anterior and posterior surfaces of the implant 100. Third, the thin film shape-memory expanse 120 is shown with micromachined fenestrations 128 which can be utilized to control localized stress-bearing capacities of the shape memory material. Both shaping elements 100 of FIGS. 4 and 6 can be rolled for introduction into the patient's eye.

Of particular interest, the capsular shaping element 100 of FIGS. 4 and 6 carries a thin film shape-memory alloy form 120 having a thickness of between about 5 microns and 50 microns. More preferably, the single layer of SMA 120 has a thickness between about 10 microns and 40 microns. The nickel titanium alloy form also is fabricated to define an $A_f$ (austhenite finish temperature) at less than about 37° C. To provide the thin film with the selected $A_f$, the element is composed of between 45-55% each of titanium and nickel. As described above, the capsular shaping element 100 then will function is it superelastic condition to cooperate with the force of contraction of the human ciliary muscle and zonular tensioning (about 1 to 3 grams of force) about the equator of the capsular sac. In other words, the contracting forces of the ciliary muscle will be sufficient to deform the intraocular device 100 to provide the lens capsule complex with a lesser axial dimension—i.e., a flatter shape. Upon relaxation of the ciliary muscle and zonular tensioning about the equator of the capsular sac, the intraocular device 100 defines recoverable strain properties that returns the element to a less stressed state wherein the intraocular device has a greater axial dimension—i.e., a more spherical or globular shape.

The capsular shaping element 100 of FIGS. 4 and 6 corresponding to the invention also can be defined by its selected dimensions and its 3-D shape for engaging and supporting the interior of the capsular sac. The outer envelope dimensions of an accommodative lens capsule are about 3.0 to 5.5 mm. about the optical axis, with a diameter ranging from about 8.0 to 10.0 mm. Thus, the outer envelope of the capsular shaping element 100 as defined by its planform and molded memory shape (its unstressed state) would match the three dimensional shape of a young still-accommodative lens capsule. The thin-film SMA form together with the capsular sac (i.e., the implant/capsule complex) defines an axial dimension AD greater than about 3 mm. when not subject to zonular tensioning forces. Further, the thin-film expanse that comprises the capsular shaping element 100 has a selected thickness and planform that demonstrates stress/strain recovery at 37° C. in response to zonular tensioning forces that flattens the axial dimension AD to less than 3.0 mm. and preferably lessens the dimension AD by about 1.0 mm. to 2.5 mm. Upon release of zonular tensioning forces, the superelastic thin film expanse 120 will rapidly return the implant/capsule complex to its unstressed state and shape.

The capsular shaping element 100 (FIG. 4) further has a thickness and planform that demonstrates stress/strain recovery at 37° C. in response to zonular tensioning forces that allows stretching of the equatorial diameter of the implant/capsule complex by greater than about 10%. More preferably, the shape memory implant demonstrates stress/strain recovery at 37° C. in response to zonular tensioning forces that allows equatorial stretching by greater than about 15%.

The ciliary muscles CM, choroid and zonular fibers each have a modulus of elasticity, and the capsular shaping element 100 in combination with the capsular sac (i.e., implant/capsule complex) defines a lower modulus of elasticity than any of these tissues to insure they do not unnaturally deform during accommodation. A capsular shaping element 100 that carries a nickel titanium alloy form, in its superelastic state when at body temperature, is the optimal material for deforming in response to zonular tension by absorbing stress and thereafter releasing the absorbed energy to return the complex of the shaping element and lens capsule to its memory shape. In one embodiment corresponding to the invention, the intraocular device carries a seamless thin-film shape memory form that demonstrates a stress/strain recovery greater than 3% at 37° C. More preferably, the thin-film shape memory form demonstrates a stress/strain recovery greater than 5% at 37° C.

Figure 7:
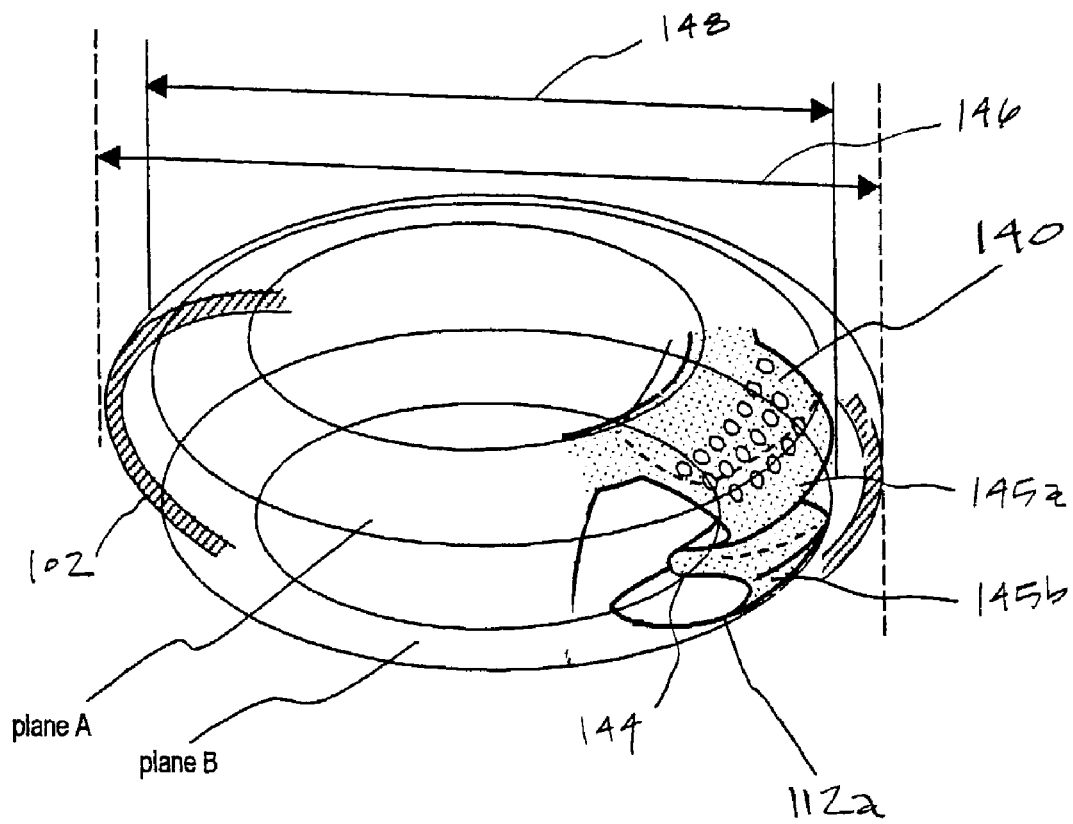
FIG. 7 is a cut-away partial view of another alternative Type "A" capsular shaping clement similar to that of FIGS. 4 and 6; this embodiment configured to provide additional stress-absorbing features and a non-elliptical equatorial region for allowing slight shrinkage of the lens capsule.

FIG. 7 illustrates, for convenience, a single peripheral arcuate body portion 112a of an alternative embodiment of capsular shaping structure 140 and engagement planes A and B. All such peripheral body portions of the shaping element would have a similar shape and function as the single element of FIG. 7. In this variant, the element 140 has an additional "S" curve or bend portion 144 in the shape memory alloy that serves two purposes. First, the additional curve 144 together with the two radially outward curves 145a and 145b can develop greater elastic energy-absorbing and energy-releasing forces than the corresponding element 100 of FIG. 4. The embodiment in FIG. 7 places the superelastic structure more directly between planes A and B. This embodiment 140 provides greater strength that the lesser hoop strength of the device of FIGS. 4 and 6 wherein a single bend portion 145 is provided in the device that urges apart planes A and B.

Figure 8A:
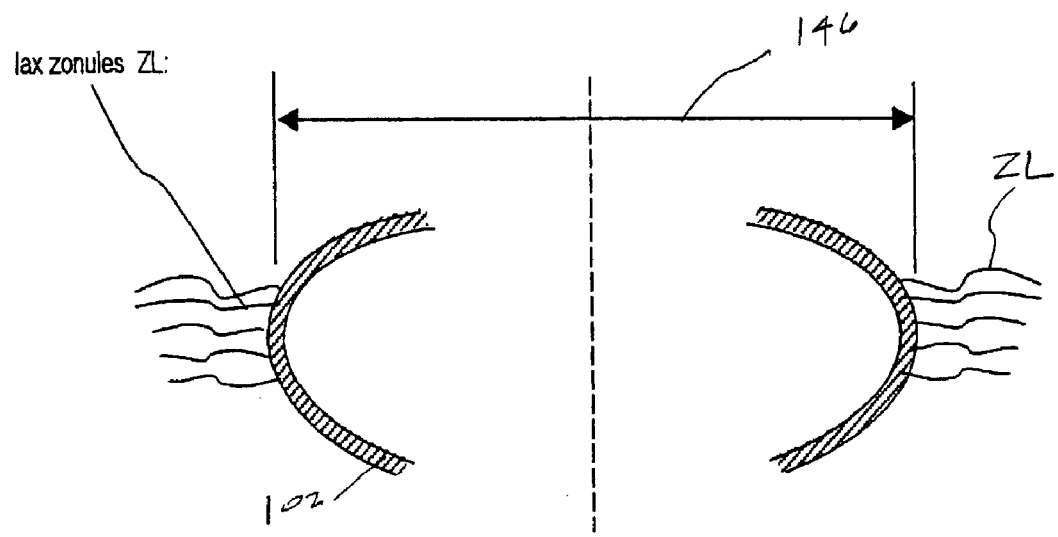
FIG. 8A is a schematic sectional view of a post-phaco lens capsule with its equatorial envelope after being shaped by the implant of FIG. 4 or FIG. 6.
Figure 8B:
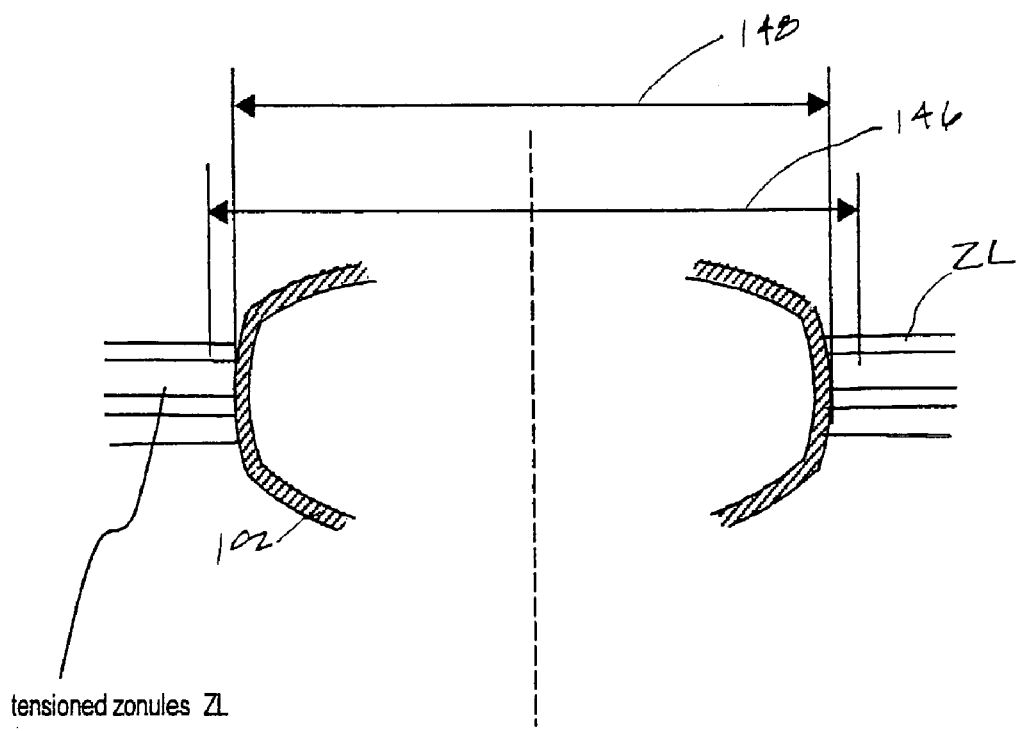
FIG. 8B is a schematic sectional view of a post-phaco lens capsule with its equatorial envelope after being shaped by the implant of FIG. 7 wherein the equatorial region is non-elliptical after capsule shrinkage to reduce laxity in the zonular ligaments.

The second advantage offered by the device 140 of FIG. 7 is that it will substantially engage the lens capsule 102 except for an equatorial band of the capsular sac. As can be seen in FIG. 7, the diameter 146 of the natural lens capsule is shown as it would be engaged and supported by the CSE as in FIG. 4 to provide a substantially elliptical or single radius equatorial region. As can be seen in FIGS. 7, 8A and 8B, the shaping element 140 of FIG. 7 defines a radially outward equatorial envelope that is substantially non-elliptical and without a radius that directly blends into the curvature of the anterior and posterior capsules. Thus, the shaping element 140 of FIG. 7 has a lesser maximum diameter 148 as indicated in FIGS. 8A-8B that will support the capsular sac in a lesser maximum diameter. It is believed that the shaping element 140 will thus support the capsular sac in an optimal open position—but allow the equatorial region of the capsule to shrink controllably after the evacuation of the crystalline lens matrix as occurs in the wound healing response and fibrotic response. This slight shrinkage of the capsular equator will then take any slack out of the zonular ligaments ZL which are believed to become lax due to lens growth over the lifetime of the patient. This will allow for more effective transfer of forces from the ciliary muscle CM to the shaping element 140 via the tightened equatorial region of the capsular sac 102.

Figure 9:
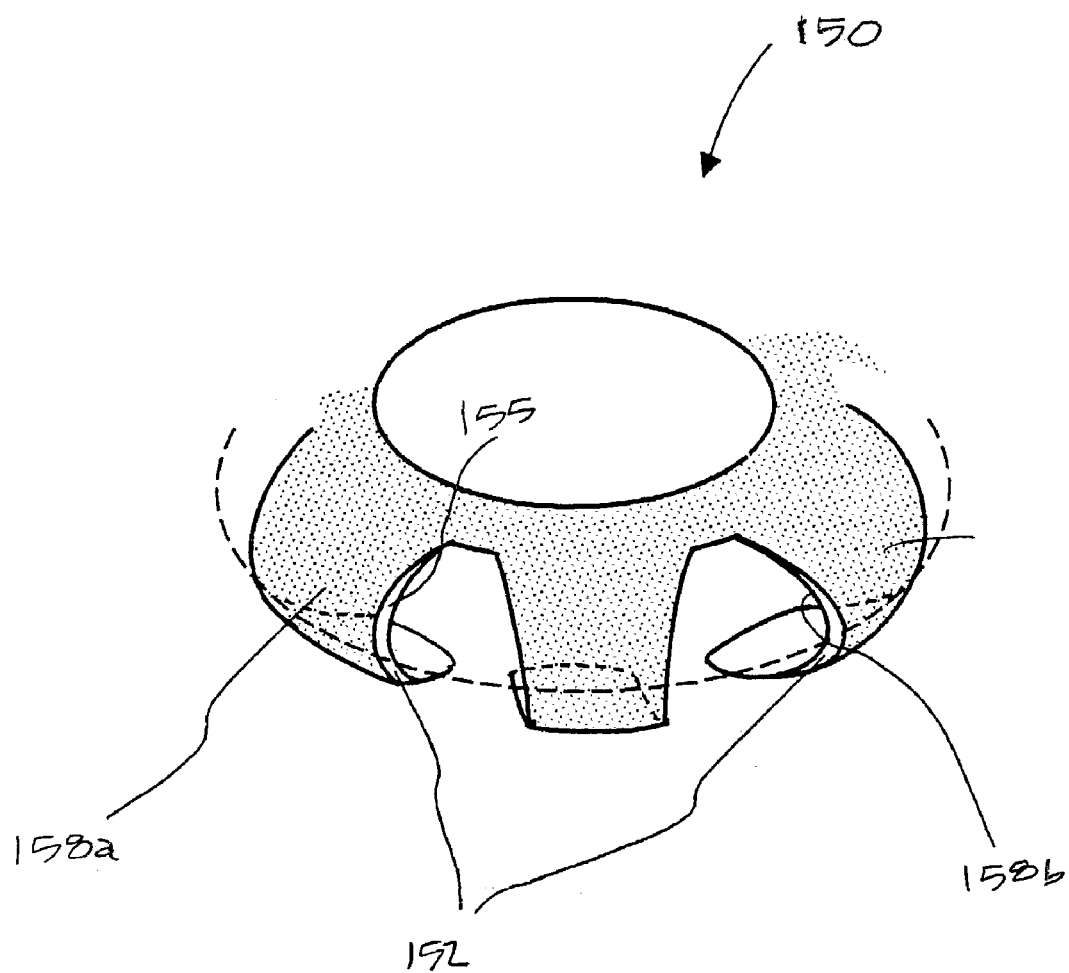
FIG. 9 is a cut-away view of an alternative Type "A" capsular shaping implant that comprises an elastic composite structure for creating enhanced stress-bearing capacity.

FIG. 9 illustrates a portion of an alternative embodiment of capsular shaping device 150 corresponding to the invention that again is adapted to engage planes A and B (see FIG. 5) of a capsular sac 102. This embodiment differs in that the peripheral arcuate portions, or the entire expanse, comprises an elastic composite material (ECM) 152 that carries first and second thin-film NiTi expanses slightly spaced apart and molded into a substantially thick polymer portion indicated at 155. The first SMA form 158*a* is similar to previous embodiments and the second layer of thin-film nickel titanium alloy is indicated at 158*b* in FIG. 9. By assembling this composite structure, the implant can provide enhanced load-bearing and response capacities that, for example, may not be attained by a single thin-film NiTi form within an implant body.

Figure 10:
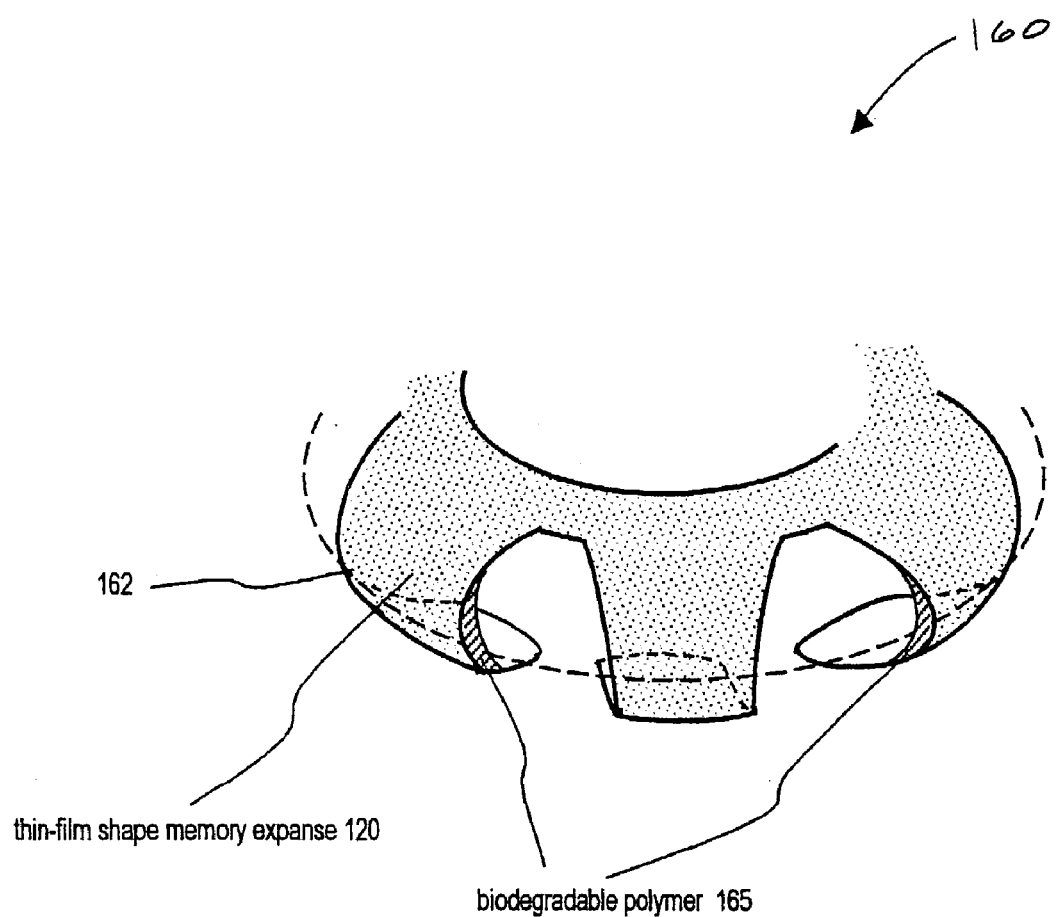
FIG. 10 is a cut-away view of an alternative Type "A" capsular shaping element that carries a biodegradable SMP or shape memory polymer for automatically altering the stress-bearing capacity of the implant following the wound healing response.

FIG. 10 illustrates an exemplary part of an alternative embodiment of capsular shaping element 160 that is similar to previous variants that engage planes A and B (see FIG. 5) of a capsular sac 102. This embodiment differs in that the equatorial portion 162 of the shaping element that flexes in response to stresses applied by the ciliary muscle carries a biodegradable shape memory polymer 165 (or any biodegradable polymer known in the art). A preferred biodegradable polymer is a PHA (polyhydroxyalkanoate), or a co-polymer of a shape memory polymer and a PHA. The purpose of the biodegradable polymer portion 165 is to selectively alter the stress (load) bearing capacity of the equatorial portion 162 of the shaping element over time. It is believed that the initial wound healing response in the capsular sac following removal of the lens matrix will apply shrinkage or fibrotic forces that will lessen after the wound healing response is over. For this reason, the inventive capsular shaping element 160 can have a first greater load-bearing capacity for selected one week to month period after implantation. The capsular shaping element 160 then can define a lesser stress-bearing capacity after the biodegradable polymer 165 has degraded—with the lesser stress-bearing capacity being optimized for cooperating with tensioning forces applied by the ciliary muscle following wound healing.

Figure 11:
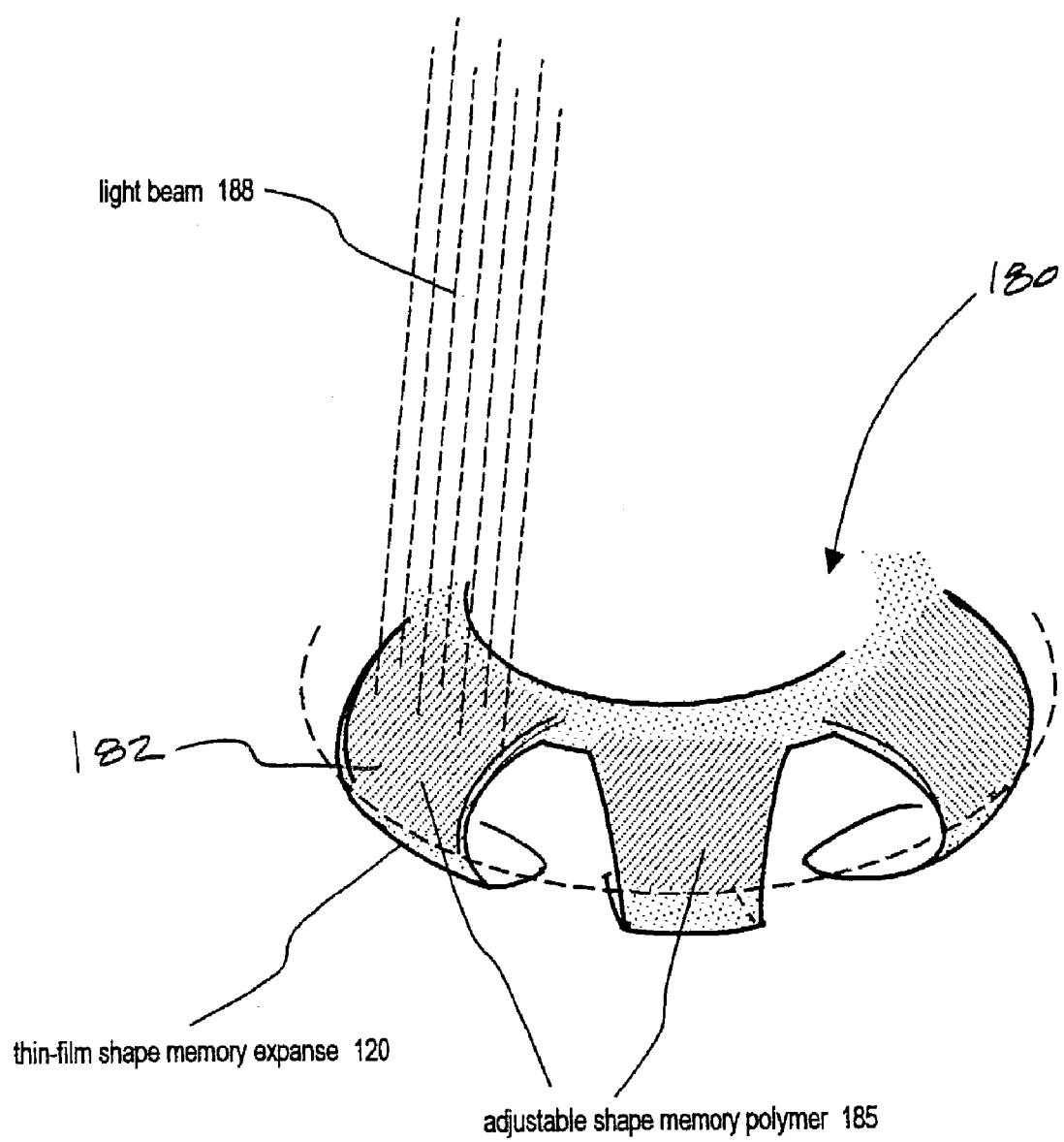
FIG. 11 is a cut-away view of another Type "A" capsular shaping element that carries an adjustable shape memory polymer (SMP) that responds to stimulus from a remote source for altering the stress-bearing capacity of the implant in the post-implant period.

FIG. 11 illustrates a portion of another alternative embodiment of capsular shaping element 180 that functions generally as the previous variants that engage planes A and B of a capsular sac 102. This embodiment differs in that the equatorial portion 182 of the shaping element that flexes in response to stresses applied by the ciliary muscle during accommodation carries an adjustable shape memory polymer 185. For example, the polymer can be a shape memory polymer that responds to stimuli from an external source to alter its modulus or shape between first and second memory shapes to selectively alter the stress (load) bearing capacity of the equatorial portion 182 of the shaping element at any time following its implantation. As described above, a shape memory polymer can be designed for photothermal modification at a selected level above body temperature to adjust modulus, flexibility, or permeability.

This aspect of the invention is shown in FIG. 11 wherein the external stimulus is light energy (e.g., a wavelength between 380 nm and 1800 nm, not limiting) that can alter the temperature or other parameter of the polymer to change its modulus or shape—which will alter the stress-bearing parameters of the composite. In the embodiment of FIG. 11, the adjustable shape memory polymer 185 is depicted as an exterior layer of the element 180 so that it is more easily exposed to a light beam 188. The light beam can be scanned and with an eye tracking system as is known in the art. The scope of the invention thus includes the use of an external energy source to modify the modulus, flexibility, permeability or other operational parameter of a non-optic portion of an intracapsular implant to optimize its resilient characteristics for enhancing the functionality of an accommodating lens system. It is believed that post-implant adjustability of such parameters will be critical for optimization of such accommodating lens systems. The modifiable polymer can be located in an region of the ophthalmic implant. The scope of the invention includes any form of stimulus, such as energy from a light source, electrical source or magnetic source.

Figure 12:
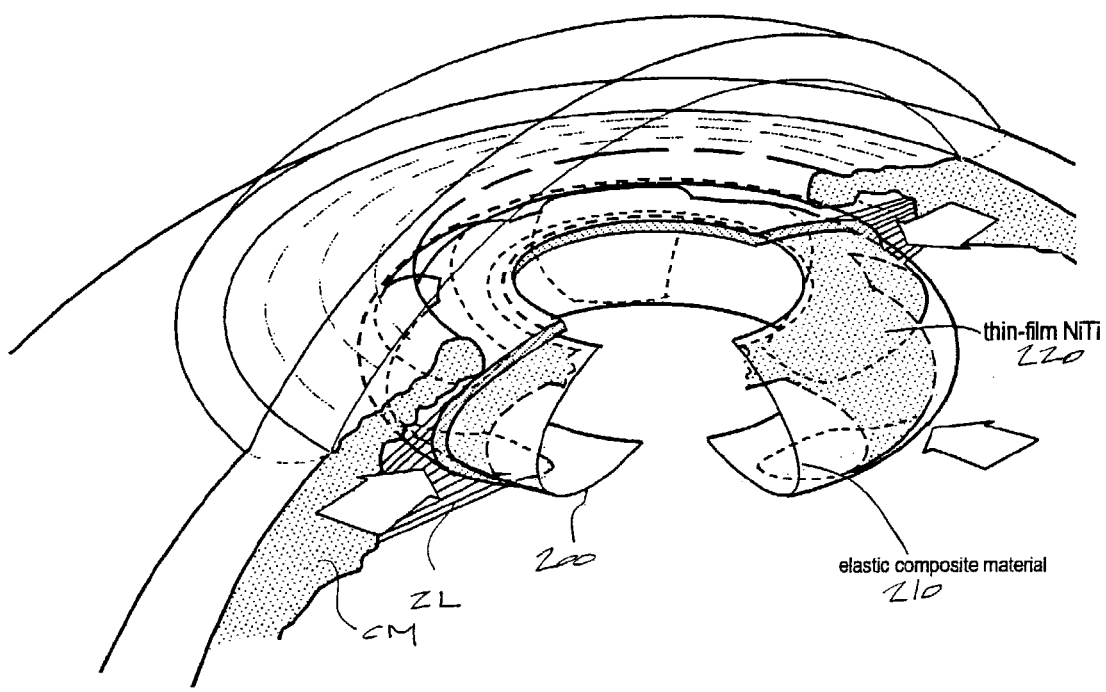
FIG. 12 is a cut-away view of Type "A" composite capsular shaping body of a thin-film shape memory alloy and an outer polymer envelope.

FIG. 12 illustrates another embodiment of capsular shaping element 200 that is similar to the implant of FIG. 4. This version differs in that the polymer portion is shown as extending substantially in a complete expanse 210 that conforms to the inner surface of the capsular sac. Preferably, the expanse 210 is of a transparent material, and in one embodiment is any biocompatible urethane, silicon-urethane copolymer or another shape memory polymer described above. In this embodiment, the thin-film nickel titanium alloy 220 is insert molded into the polymer body portion to provide the stress-bearing capacity of the shaping element.

In all of the above described embodiments, the capsular shaping element and the remaining capsule sac is adapted to mimic a natural lens capsule in balancing its energy-absorbing and energy-releasing characteristics with the forces applied by the ciliary muscle. The capsular shaping element will thus prevent atrophy of the ciliary muscle and allow it to cooperate with, and adjust, the next optional component of the invention which is a cooperating independent IOL or an integrated optic element.

Still, it should be appreciated that the capsular shaping devices of FIGS. 4 to 11 comprise an important ophthalmic implant innovation. The capsular shaping devices will maintain the capsule as an open and viable structure, thus allowing the ophthalmologist to insert and replace any IOL as required to adjust the lens power over the lifetime of the patient. Explanting an in-the-sac IOL is not simple with current IOLs since the designs are intended to be shrink-wrapped in the capsule to maintain lens centration. In the future, it is likely that ultra-thin SMA haptics with thin optics will allow the development of replaceable IOLs that can be inserted and removed with a sub-1.0 mm. entry through the cornea making the IOL exchange an atraumatic procedure. It is believed that IOL replaceability will become a needed refractive option in clear lensectomy procedures to treat presbyopia, wherein over the lifetime of the patient a refractive lens change may be required due to refractive drift, or lens exchange for a new lens technology may be desired (e.g., for a wavefront corrected lens).

Figures 13A, 13B:
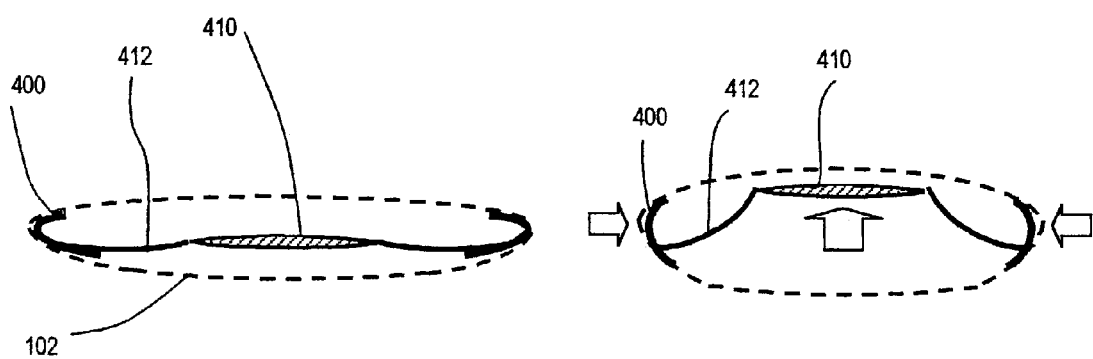
FIGS. 13A-13B are sectional schematics of a Type "B" capsular shaping element with integrated optic element showing disaccommodative and accommodative positions, respectively.
Figure 14:
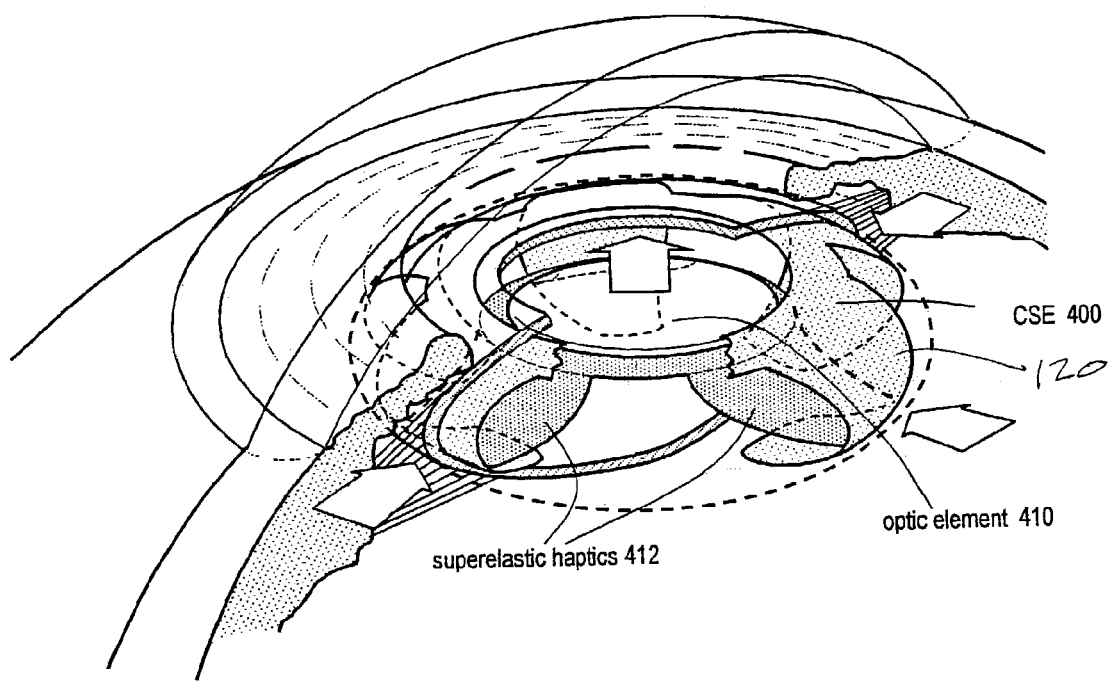
FIG. 14 is a cut-away view of the Type "B" IOL of FIGS. 13A-13B.
Figure 19:
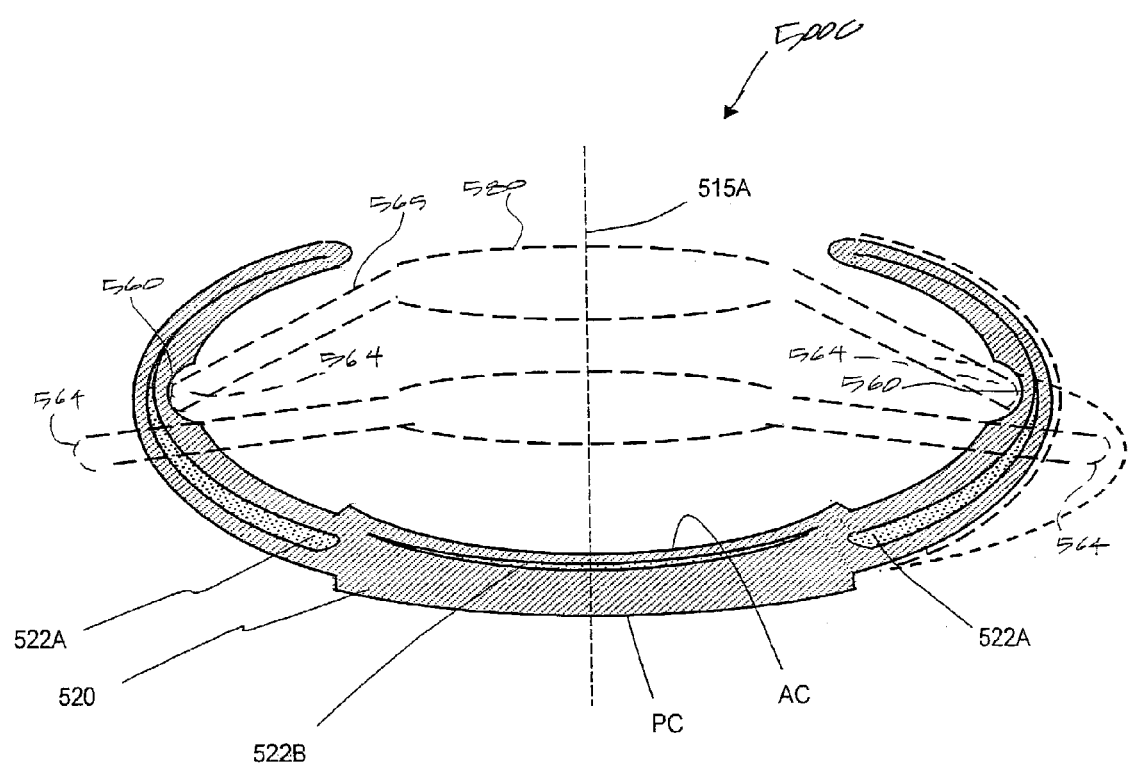
FIG. 19 is a sectional view of an alternative intraocular device similar to FIG. 16A showing a drop-in IOL in phantom view engaged with the implant device of FIG. 16A.

B. Type "B" Implantable Intraocular Devices. The Type "B" intraocular devices generally combine any of the Type "A" capsular shaping structures of the invention with an integrated optic portion to thereby provide an integrated accommodating IOL system. FIGS. 13A-13B and 14 illustrate a various views of a capsular shaping body 400 with shape memory alloy form 120 therein similar to that of FIG. 4 with an integrated optic element 410 coupled to the shaping element 400 by haptic portion 412. The haptic portions 412 (i) can be fixedly coupled to body 400, (ii) can be adapted to resiliently press outwardly to self-locate about the equator of the body 400, or (iii) can be adapted to cooperate with an engagement element in body 400 as shown in FIG. 19. FIGS. 13A-13B illustrate how changes in the shape of the CSE portion 400 are captured to cause the optic element 410 translate anteriorly lens to provide additional focusing power. Thus, the IOL system of FIG. 14 provides a substantially true accommodating lens system based on the mechanism of lens translation. In use, psuedo-accommodative vitreous displacement also would be enhanced by the implant that presents a substantially large convex body surface toward the vitreous, which would be an improvement over the reduced surface area of a shrink-wrapped posterior capsule. In this embodiment, the haptic portion 412 again is a superelastic NiTi form encased in a polymer that is further molded to transition to a central foldable lens as in known in the art.

Figure 15B:
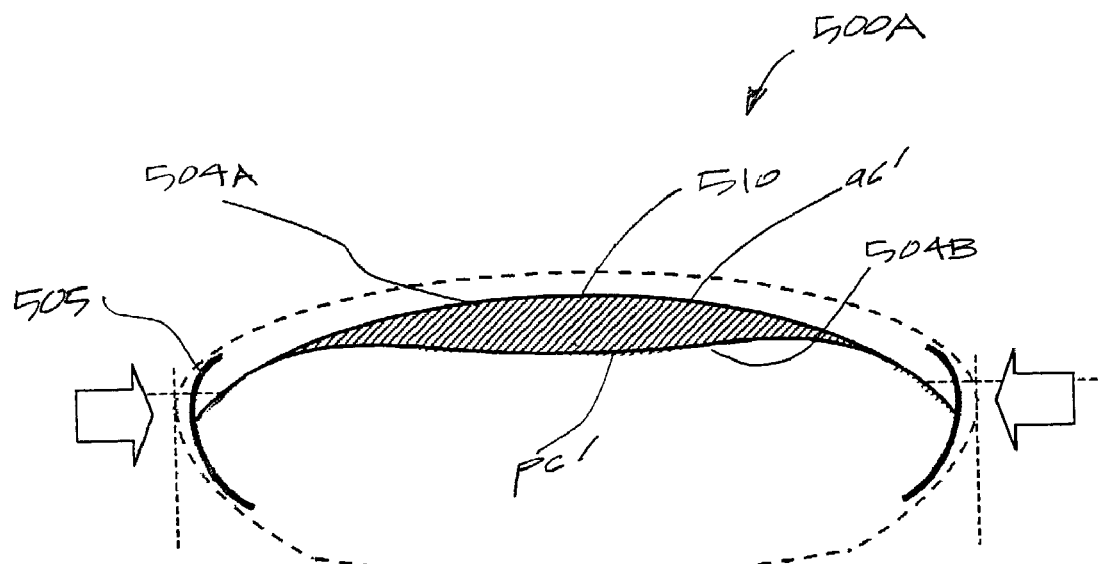
FIGS. 15A-15B are sectional schematics of another Type "B" capsular shaping element with integrated fluid-filled adaptive optic element.
Figure 15A:
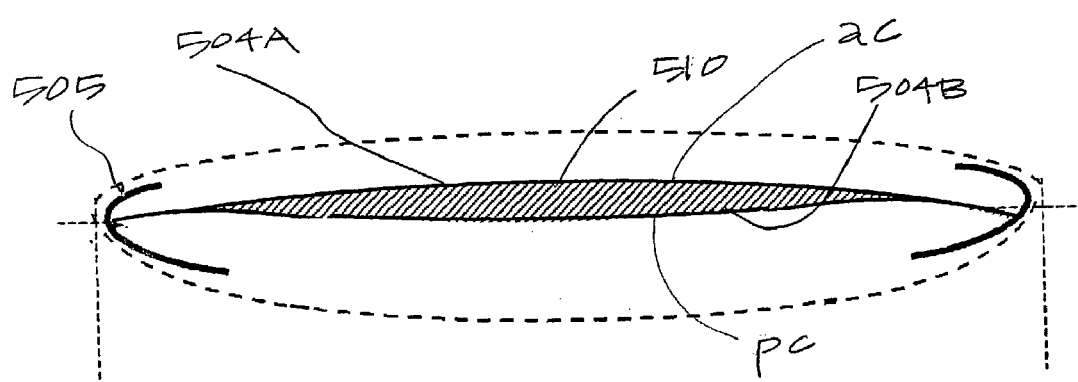
Figure 15C:
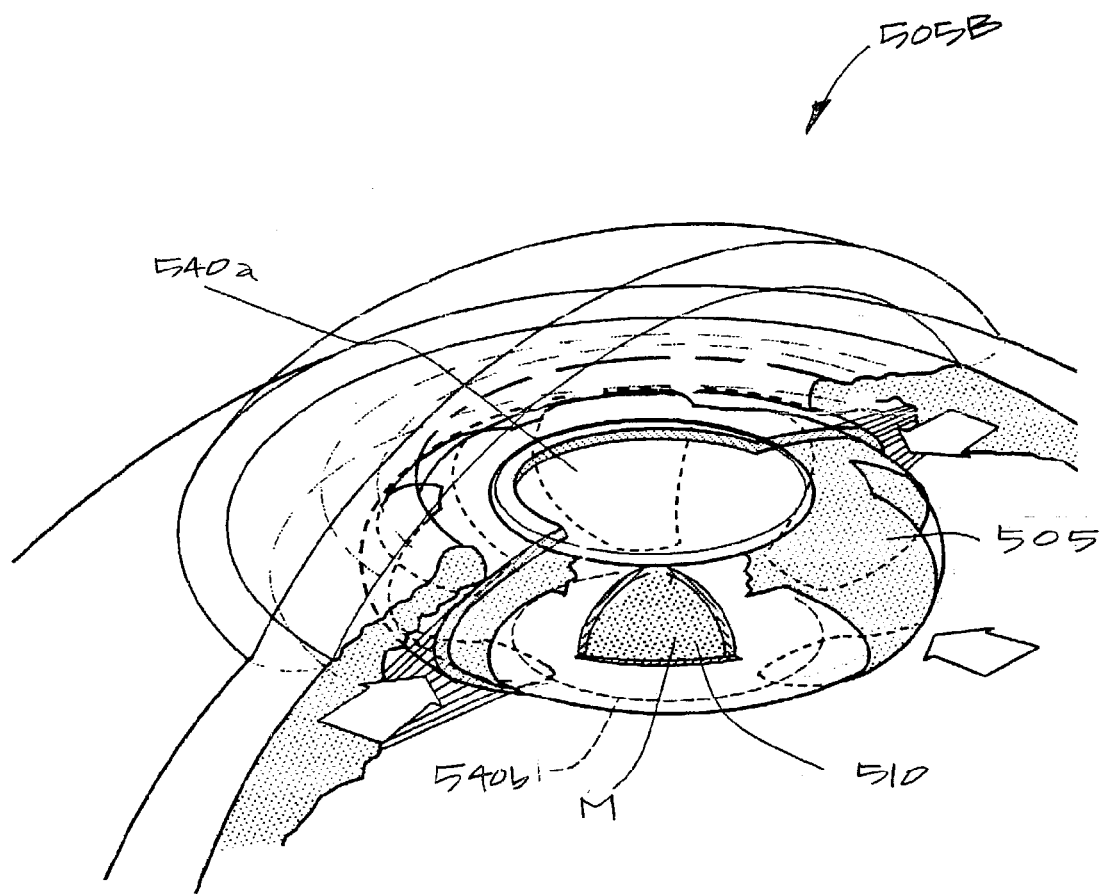
FIG. 15C is a view of another Type "B" capsular shaping body with and integrated gel-filled optic element that substantially occupies the volume of the capsular sac.

FIGS. 15A-15B illustrate views of an alternative embodiment of integrated IOL 500A with a capsular shaping element portion 505 having NiTi form 120 therein together with an integrated optic portion 510 coupled to the shaping element 505 by an intermediate fixed coupling portion indicated at 502. In this embodiment, the optic portion 510 is a flexible fluid-filled optic with an anterior deformable surface layer 504A and an optional posterior deformable surface layer 504B that contains a displaceable fluid or gel media M therebetween. In such an adaptive optic embodiment, each surface 504A and 504B can comprise a lens element with the displaceable media having any index, or the surfaces 504A and 504B can contain an index-matched displaceable media M therebetween to effectively function as a single optic element. As can be seen in FIGS. 15A-15B, the change in shape of the capsular shaping portion 505 will alter the curvature of a deformable lens surface, or both surfaces, ac and pc to ac' and pc' while translating the optic anteriorly and increasing the thickness of the lens—all of which mimic a naturally accommodating lens to provide lens accommodation. FIG. 15C shows an alternative integrated IOL system 500B wherein the peripheral capsular shaping body 505 is as described previously with a SMA form therein to provide the capsular sac with the desired strain-absorbing properties. In this embodiment, the central optic portion 510 again is a flexible fluid-filled optic but with foldable (but non-adaptive) anterior and posterior lens elements 540a and 540b that contain a displaceable fluid or gel media M therebetween, either index matched or non-index matched. In the embodiment of FIG. 15C, the anterior and posterior lens elements 540a and 540b move apart during accommodation to increase lens power. In essence, this system emulates a natural lens capsule.

Figure 16A:
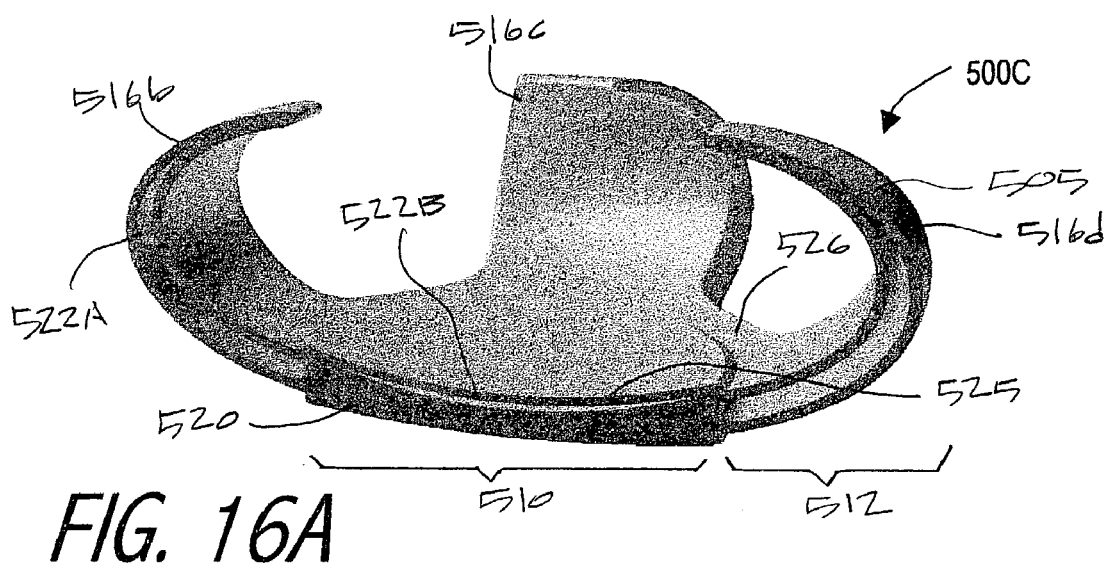
FIG. 16A is a sectional view of another Type "B" capsular shaping element with a posterior negative power adaptive lens element with fluid displacement means for altering the lens power.
Figure 16B:
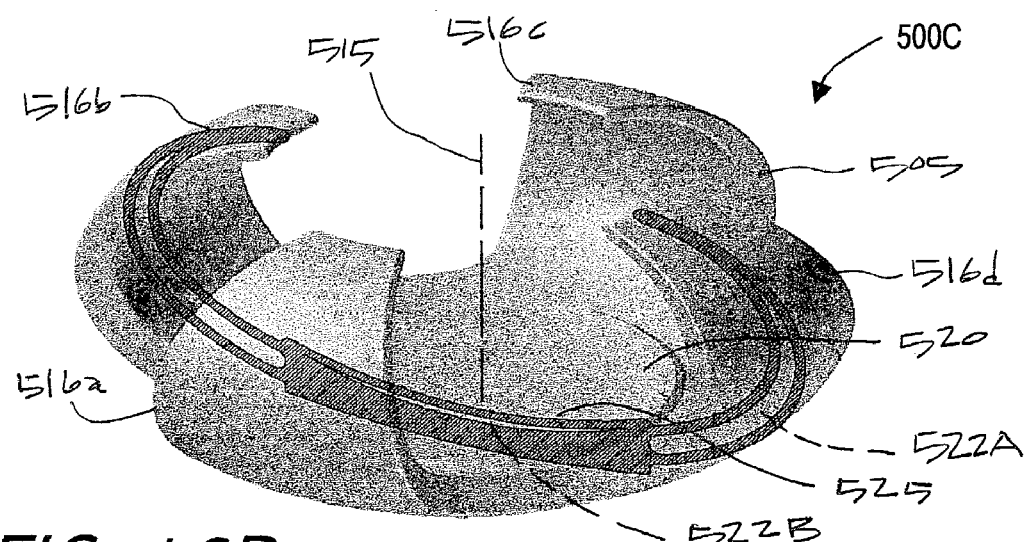
FIG. 16B is a perspective view of the implant device of FIG. 16A.

FIGS. 16A-16B are views of a Type "B" implant device 500C that has a capsular shaping body portion 505 together with a refined microfluidic system for causing fluid flows into a deformable adaptive optic portion 510 from a peripheral non-optic portion 512 that is adapted to engage the capsular sac. As can be seen in FIG. 16B, the capsular shaping body 505 has a plurality of peripheral arcuate extending elements 516a-516d that can number from about 3 to 12. Alternatively, the body portion 505 can extend 360° about the implant, or a plurality of elements with an intermediate thin sheath element can extend 360° about the implant. The implant defines an open anterior central region.

In the implant 500C of FIGS. 16A-16B, the peripheral capsular shaping portion 512 carries several features that can assist in causing a lens element or elements provide accommodative effects. The peripheral body portion 512 transitions to an annular body portion 526 that carries a posterior lens 520 with a deformable anterior surface 525 that can be controllably deformed by the flow of an index-matched fluid media M to and from an interior space or chamber indicated at 522B. The lens is deformed by flow from at least one peripheral chamber 522A in the peripheral elements 516a-516d. The fluid flows are designed to occur when elements 516a-516d are deformed from their memory shape (FIGS. 16A and 20A) to a temporary shape (FIG. 20B) by zonular tensioning. The memory shape of the body 505 again is provided by a superelastic NiTi form embedded therein (not shown). The peripheral body portion 512, as in all earlier embodiments, is adapted to deform under about 1.0 to 3.0 grams of applied force about the equatorial region of the implant.

In one embodiment as depicted in FIG. 16A, the lens 520 has a negative power and is adapted to cooperate with an independent positive power lens that is implanted in the open central portion of the capsular shaping body 505 as shown in phantom view in FIG. 19. It should be appreciated that the system of the invention can be designed for fluid flows to or from the central optic to add or subtract power to a positive power lens, a negative power lens or a plano lens.

Figure 17:
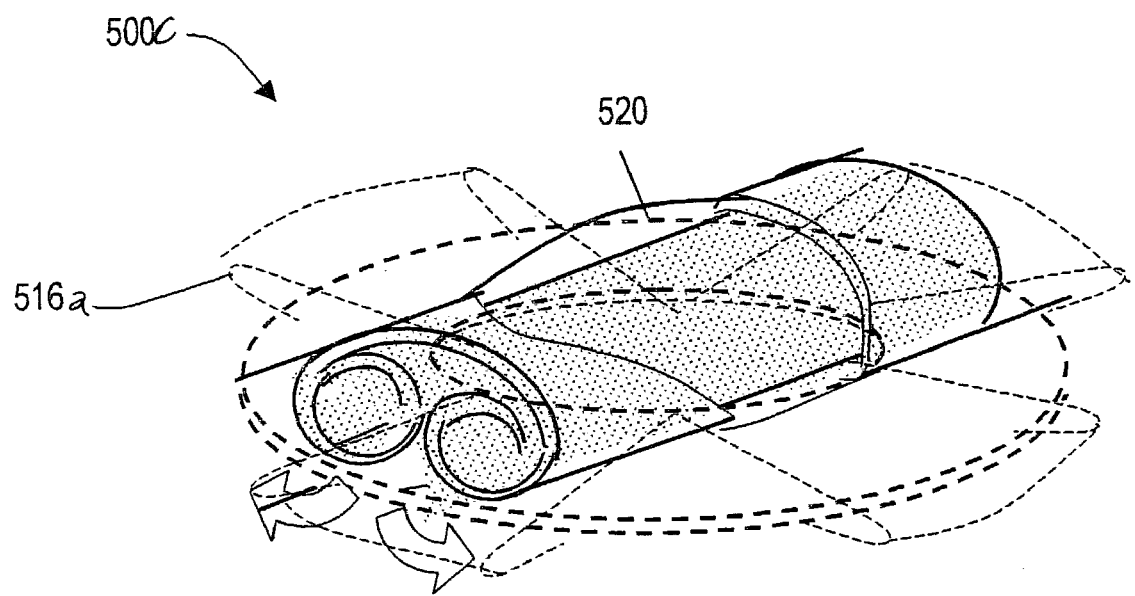
FIG. 17 is a view of a Type "B" intraocular device of FIG. 16A showing a method of rolling the device for introduction into the eye, the body of a shape memory polymer (SMP) encasing a shape memory alloy form.

FIG. 17 is a view of the intraocular device of FIGS. 16A-16B showing a method of rolling the device for introduction into the eye, wherein the body 505 is an assembly of a superelastic SMA form insert molded into a shape memory polymer, and the SMP then is compacted to a temporary shape. In such a preferred embodiment, a thin film NiTi form or a NiTi wire form together with the polymer component would be very thin. The peripheral body portion would be in the range of 25 to 100 microns in thickness, which is suitable for rolling or folding as shown in FIG. 17.

Figure 18:
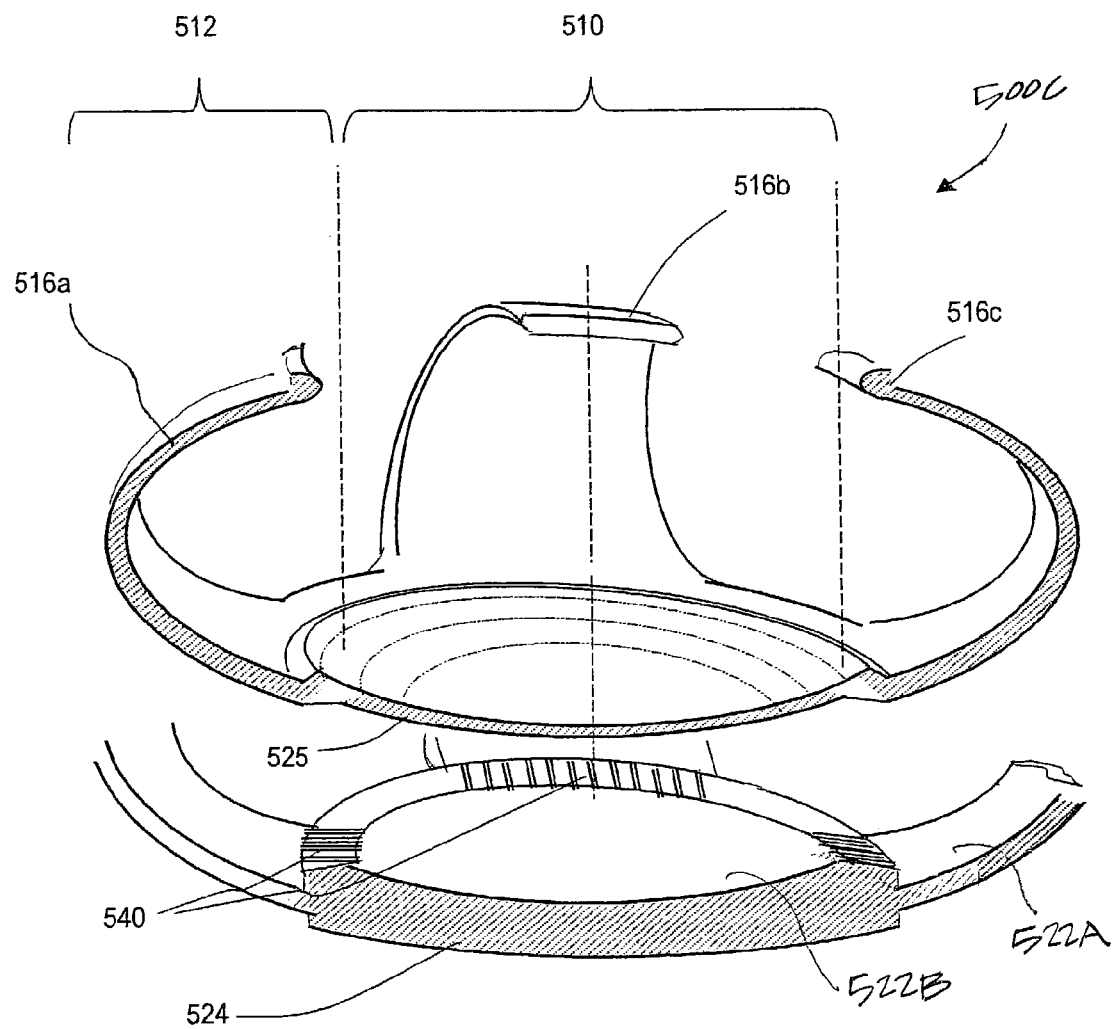
FIG. 18 is an exploded view of the two components of the device of FIG. 16A, showing flow channels between the interior chambers of the peripheral non-optic portion and the optic portion.

FIG. 18 is an exploded view of a manner of fabricating the implant 500C of FIGS. 16A-16B showing two components 532a and 532b de-mated with molded-in flow channels 540 that would communicate between the interior chambers of the optic portion and peripheral non-optic portion. In this embodiment, the deformable lens layer 525 is substantially thin while base potion 524 of the lens is less deformable or preferably non-deformable. The superelastic SMA form 120 (see FIG. 4) is molded into either or both polymer components 532a and 532b. A fluid media M is inserted into the chambers during or after bonding together the polymer components 532a and 532b.

FIG. 19 is a sectional view of an intraocular device 500C similar to that of FIG. 16A showing that the body 505 carries an engagement structure indicated at 560 for cooperating with and positioning the engagement ends 564 of haptics 565 that carries lens 580 (phantom view). FIG. 19 further shows how the optic 580 would translate to provide an accommodative effect as in the previous embodiment of FIGS. 13A-13B and 14.

Figure 20A:
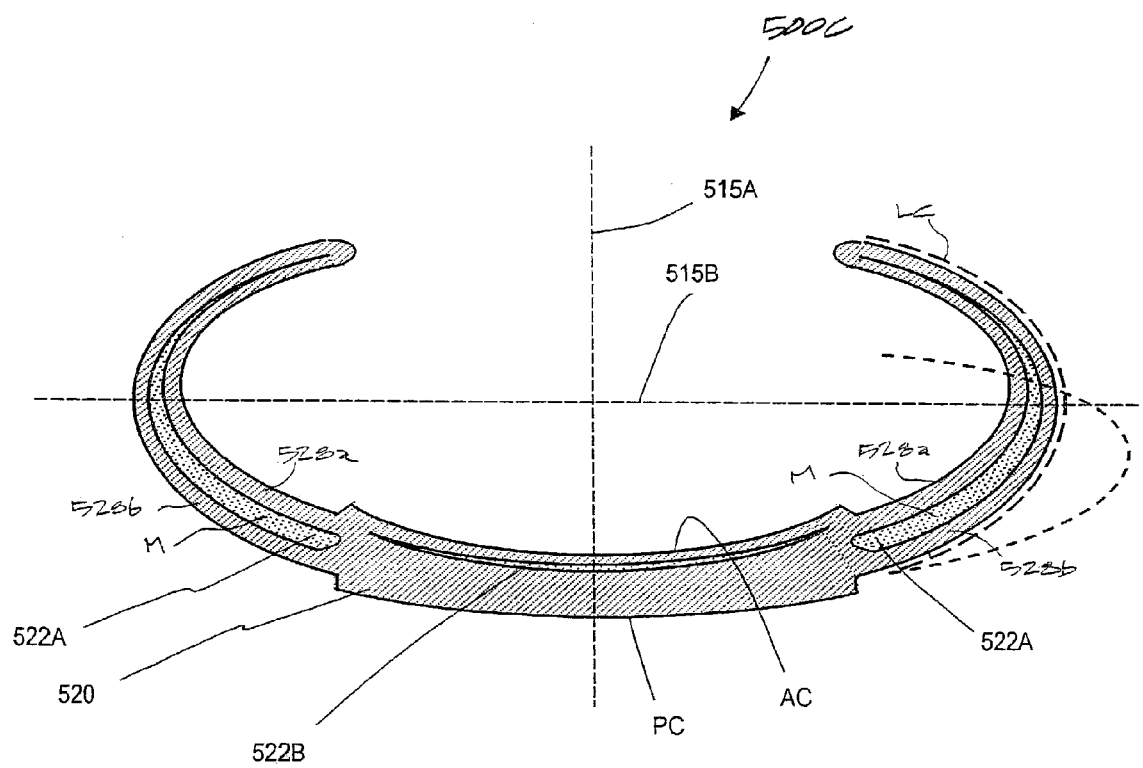
FIG. 20A is a sectional view of the intracapsular device of FIG. 16A at, or urged toward, its memory shape as when implanted in a capsular sac.
Figure 20B:
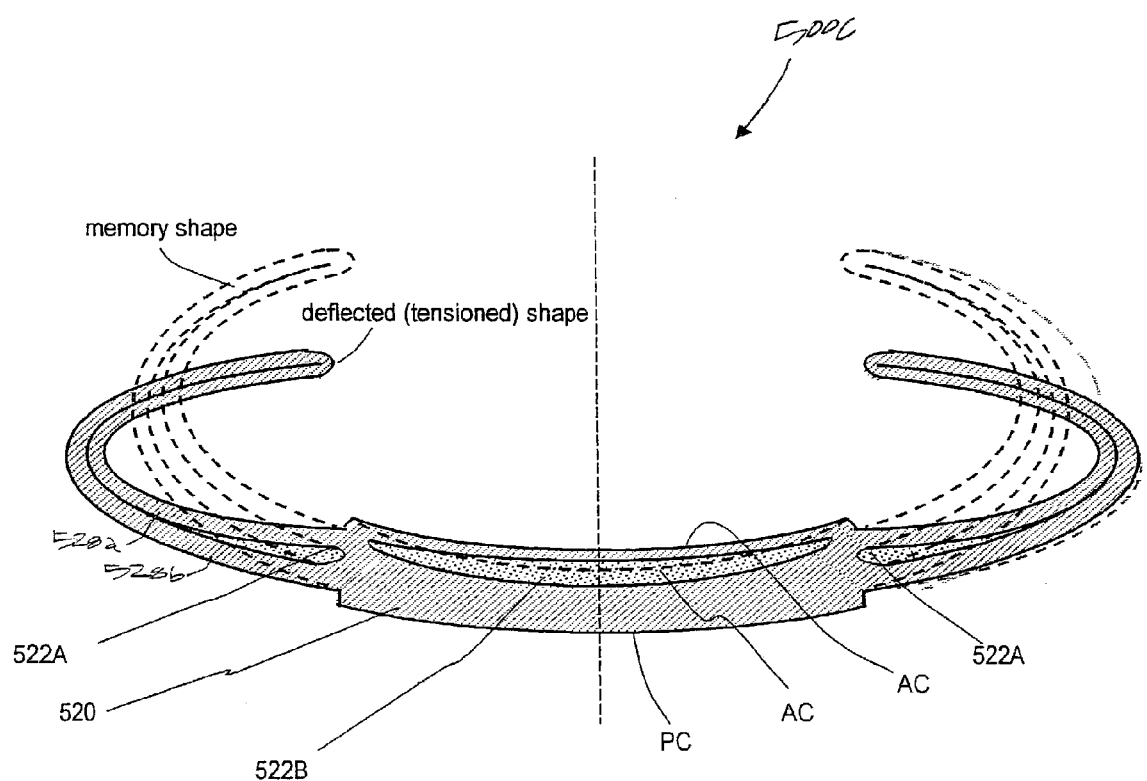
FIG. 20B is a sectional view of the intracapsular device of FIG. 20A deformed toward a temporary shape showing a flow of fluid from the peripheral non-optic portion to the optic portion to alter the power of the lens.

Now turning to FIGS. 20A-20B, the movement of the peripheral capsular shaping body 512 from its memory shape to a temporary shape will cause compression of wall portion 528a against wall portion 528b to displace fluid media M from interior chambers 522A (collectively) to the interior space 522B in the lens 520 to alter it curvature to AC' from AC. The scope of the invention includes any of a variety of mechanisms and cavity shapes in the non-optic portion 512 that are compressed to cause fluid media flow to the optic portion. Also, the scope of the invention includes mechanisms and cavity shapes in the non-optic portion 512 that are expanded to cause fluid media flow from the optic portion. The interior space in the lens can be (i) centrally located or (ii) peripherally located in an annular region to thereby allow the deformation of the surface to add or subtract power in a plano lens, positive power lens or negative power lens. The peripheral extending portions 516a-516d carry NiTi forms either of a thin film expanse or wire forms to induce the portions 516a-516d toward the memory shape as well as return the chambers 522A to a "memory" volume. The sectional view of FIG. 16A illustrates the capsular sac and implant at, or urged toward, its memory shape as when implanted in a lens capsule LC (reference letter LC indicating the interior of the lens capsule). It can be seen that a substantial volume (first volume) of fluid media M is within the peripheral non-optic portion and chambers 522A therein. In this untensioned or memory state, there is a limited volume of media M in the interior space 522B of the lens.

Figure 21:
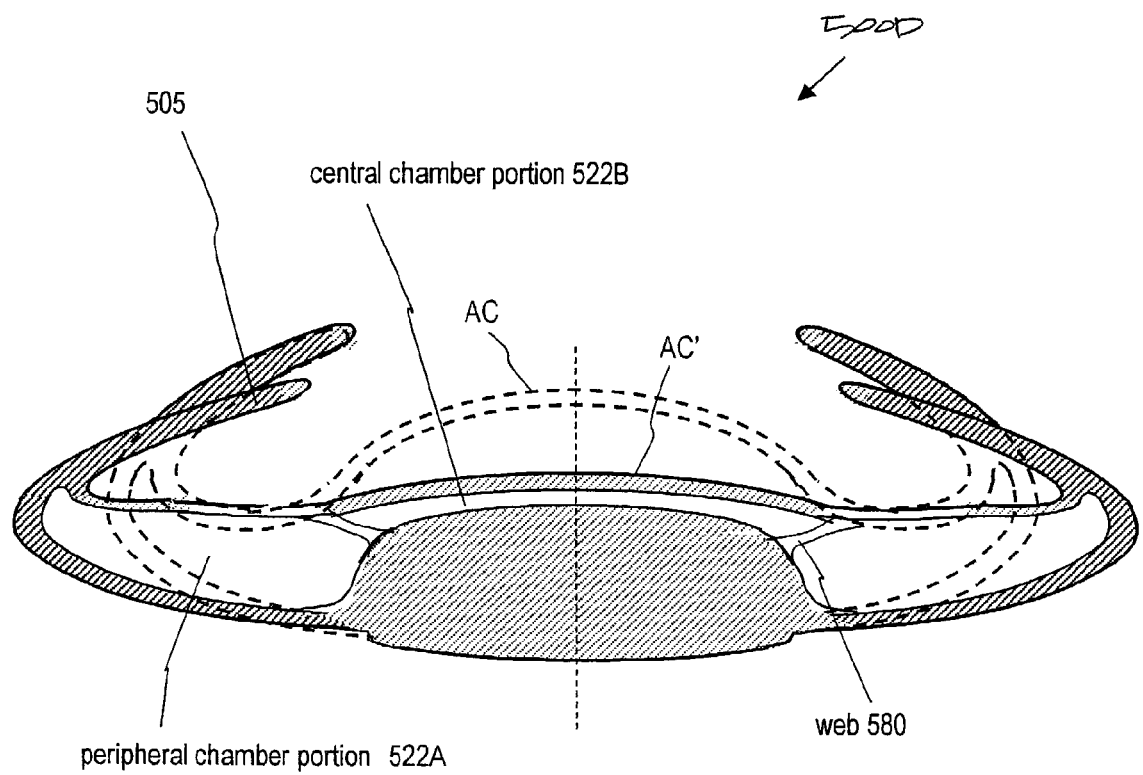
FIG. 21 is a sectional view of a capsular shaping body and adaptive bi-convex optic with communicating peripheral and central chamber portions showing accommodative and disaccommodative shapes.

In a disaccommodative state, referring to FIG. 20B, the sectional view shows the body portion 512 in a tensioned collapsed (temporary) shape when zonular tension flattens the lens capsule and collapses the axial dimension of the implant along optical axis 515. It can be seen that the axial collapse of implant causes compression of the peripheral chambers 522A and moves a volume of fluid media M into space 522B of the lens 520. The increased fluid pressure in the space 522B thereby deforms the lens surface 525 and subtracts from the negative power of the lens. It can be easily understood how this added fluid pressure can be used to reshape a lens to make a deformable surface, whether (i) to make the curvature steeper or flatter with a central interior space 522B or an annular interior space 522B; (ii) to add power or subtract power; or (iii) to move a piano element away from non-refractive parameters toward either a positive or negative power. It is important to note that the method of the invention includes providing a large fluid volume in the peripheral chambers 522A when compared to the lens chamber 522B to thereby provide hydraulic amplification means for transducing and amplifying the mechanical flexing of the body portion 512 to maximize lens deformation. FIG. 21 is a sectional view of an alternative adaptive optic device 500D wherein flexure of the peripheral portion 512 to a flatter shape impinges on the volume of the peripheral chamber portions 522A to subtract from the power of a bi-convex lens by adding an index-matched fluid media to the chamber portion 522B within the lens 520. It can be seen that the deformable surface 525 is restrained at the annular optic periphery by webs 580 to control the shape change in response to fluid media flow.

Figure 22:
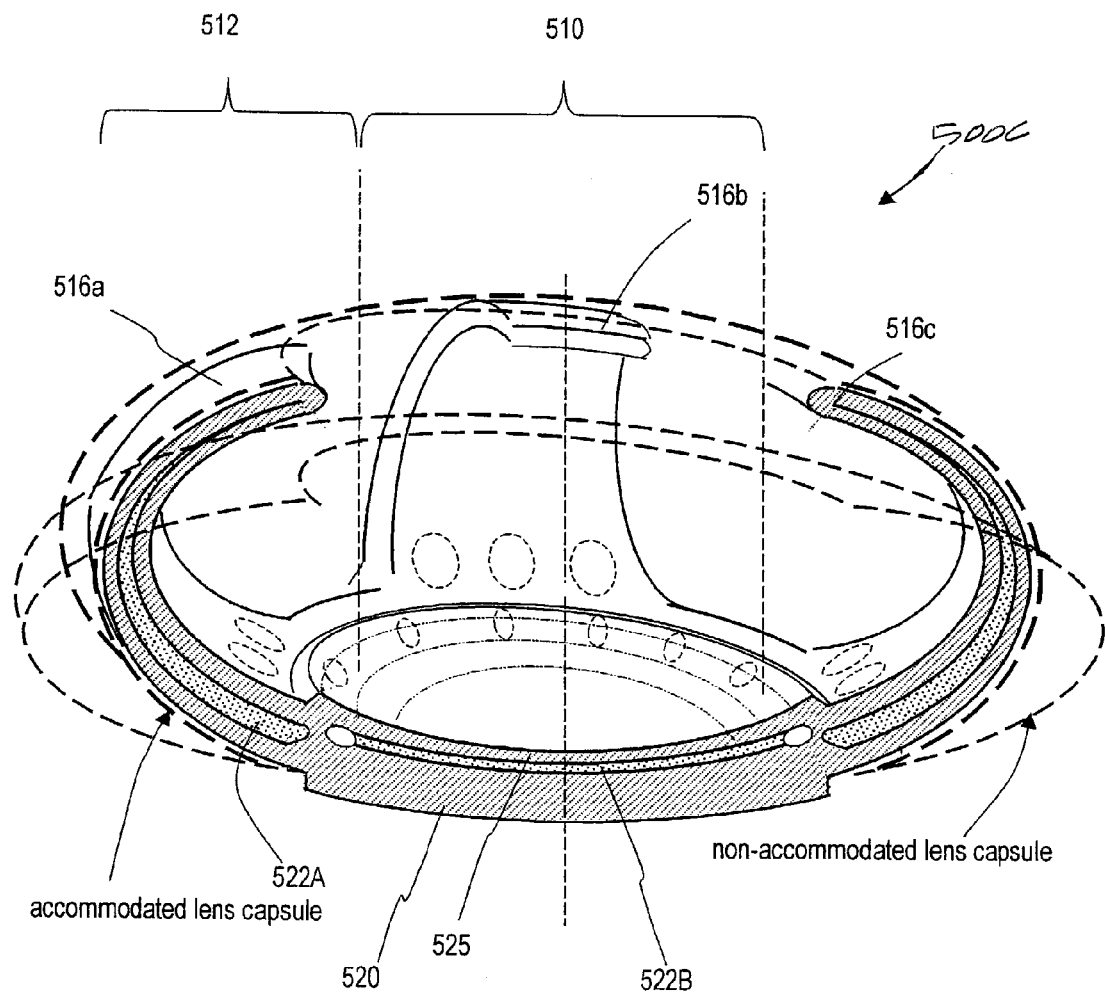
FIG. 22 is a cut-away view of an alternative intraocular device similar to FIG. 16A illustrating a plurality of regions of a shape memory polymer adjacent to an interior space that are responsive to an external energy source to alter fluid flows and the dynamics of fluid displacement in the optic portion.

In any design of capsular shaping body or for an accommodating lens system, it may be necessary to provide post-fabrication adjustment means for (i) adjusting the flexibility and response to the peripheral body's deformation after implantation, (ii) the exact shape of a dimension of the implant to engage the lens capsule, (iii) the amplitude of accommodation, as well as (iv) providing for adjustment of lens optic parameters. To provide for such adjustments, FIG. 22 shows a cut-away view of a capsular shaping body and lens similar to the embodiment of FIG. 16A. A plurality of regions 588 of the capsular shaping body are of a shape memory polymer that is disposed adjacent to an interior space or chamber in the implant. Each SMP portion is responsive to an external energy source that cause it to swell to thereby impinge on the chamber to reduce its volume (increase internal fluid pressure). While the regions are discrete and spaced apart in FIG. 22, they also may be annular or comprise a thin layer of a polymer expanse. Similarly, the SMP regions (not shown) may extend within broad surface regions of the capsular shaping body to alter its modulus or flex characteristics. In particular, altering the mechanical properties of the polymer body component can offset and cooperate with the properties of the NiTi form 120 therein to alter the resilient characteristics of the composite.

Figure 23:
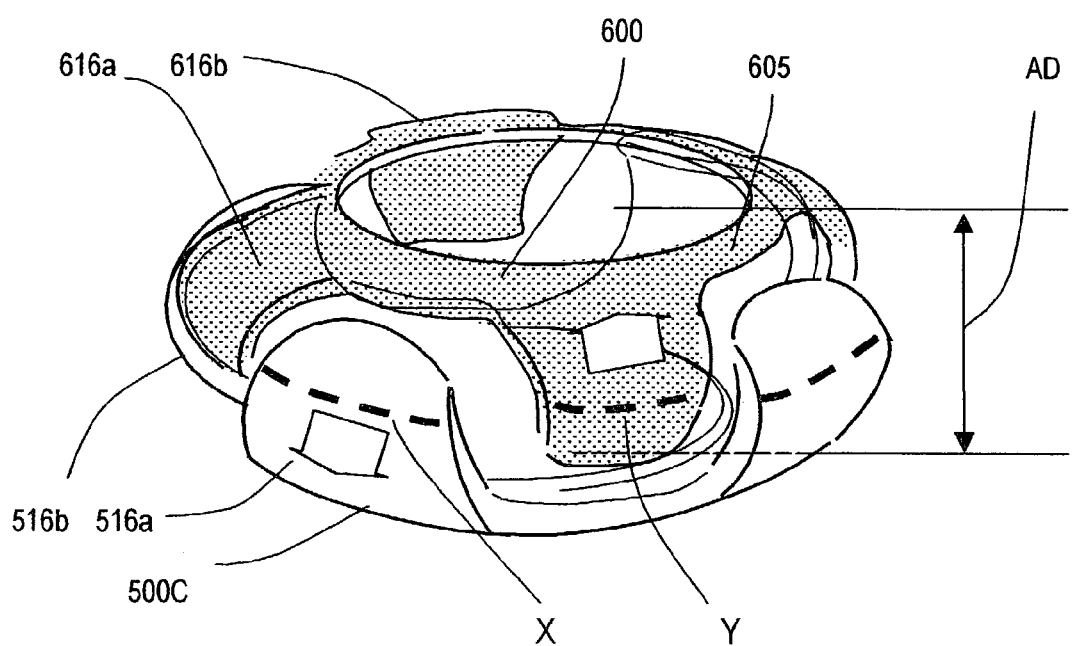
FIG. 23 is a perspective illustration of a capsular shaping system that utilizes first and second cooperating independent devices (in an accommodative shape), each similar to the device of FIG. 16A, one device for engaging the posterior capsule and a limited equatorial capsular region and the second device adapted for engaging only the anterior capsule and a limited equatorial region.
Figure 24:
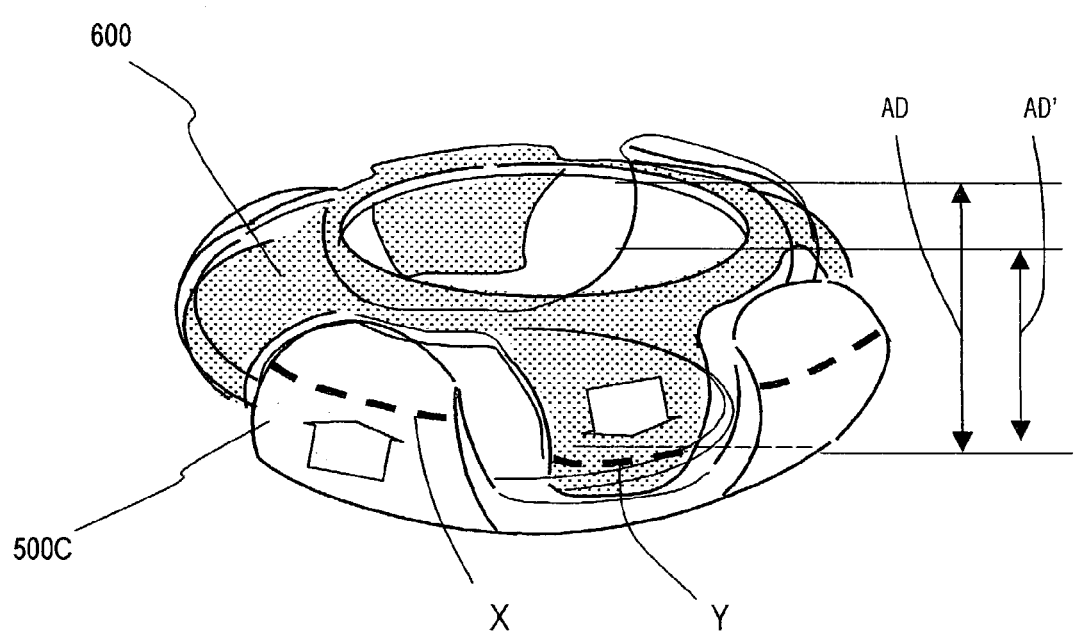
FIG. 24 is a perspective view of capsular shaping system of FIG. 23 with the cooperating independent devices in a disaccommodative shape.

FIGS. 23-24 illustrate a capsular shaping system with a first shaping body 500C similar to that of FIG. 16A together with a second independent inverted shaping device 600. The first device is adapted to engage the posterior capsule and a limited equatorial region (cf. FIG. 16A). The second device 600 is adapted for engaging only the anterior capsule and a limited equatorial region. The second shaping device 600 has a number of extending portions 616a-616d that cooperate with and are spaced between the corresponding portions of the first device 500B when implanted in a capsular sac. The second device 600 further defines an annular portion 605 that transitions into the extending portions 616a-616d. Of particular interest, the use of first and second independent shaping devices for engaging the anterior and posterior capsules with independently responsive elements allows the lens capsule to respond to zonular tensioning and de-tensioning more like a natural lens capsule. This can be understood by reference to equatorial indicator markings on the implants in FIGS. 23 and 24 which show the device in accommodative and non-accommodative shapes, respectively. It can be seen that the axial dimension of the capsular complex moves from AD to AD' as the system moves toward a disaccommodative shape (FIG. 24). It can easily be understood (see arrows) that movement of the capsule complex toward its non-accommodative equatorial dimension will cause the extending portions 516a-516d and extending portions 616a-616d to adjust or slip relative to the equatorial plane of the complex. In FIGS. 23 and 24, equatorial indicator markings X and Y on the respective extending portions 516a-516d and extending portions 616a-616d are shown in different alignments with one another when the lens capsule adjusts between accommodative and non-accommodative shapes. Of particular interest, the independent cooperating capsular shaping bodies will prevent the implant from simply forming a hinge at the equatorial apex of the device. By utilizing such a design feature, a greater amplitude of capsular shape change can be achieved for a given amplitude of zonular tensioning. It should be appreciated that the independent devices 500B and 600 can be coupled by thin flexible membranes (not shown) and fall within the scope of the invention, wherein the posterior and anterior shaping bodies still substantially provide the desirable functionality described above to prevent the hinge effect at the equatorial apex of the device.

Figure 25:
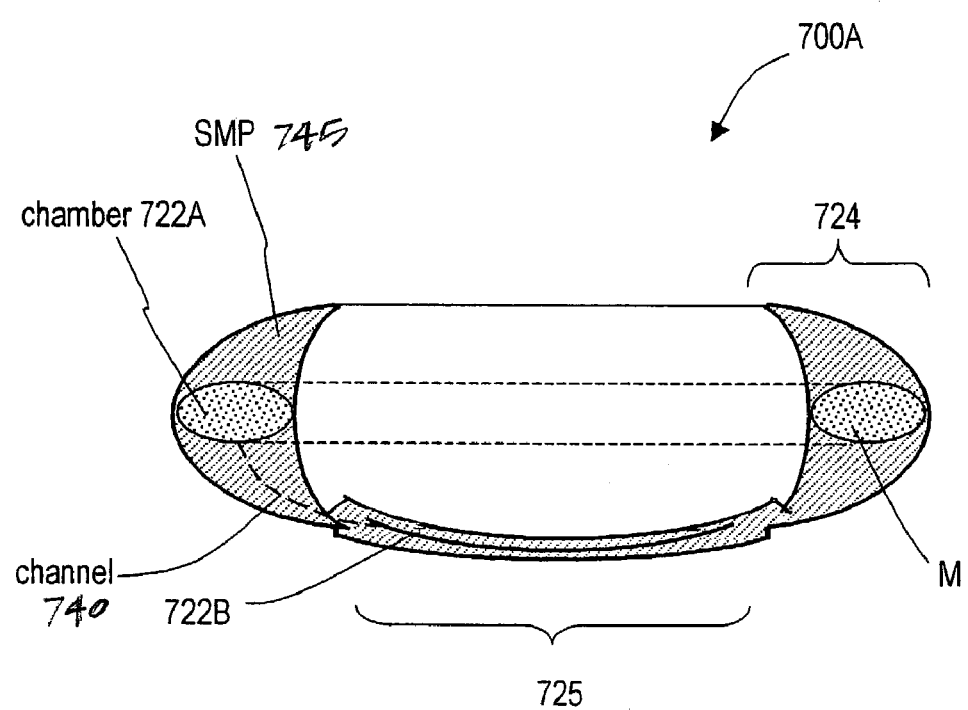
FIG. 25 is a sectional view of an alternative intracapsular implant and adaptive optic with a shape memory polymer peripheral body that carries and interior fluid-filled chamber.

The previous embodiments have illustrated peripheral body portions that are substantially thin and provided with an elastic response due to the superelastic SMA form 120 insert-molded therein. Embodiments of adaptive optic lens systems as described above are possible without, or with less reliance on, a superelastic shape memory alloy form in the implant. In order to provide a polymer peripheral body portion with suitable resilient characteristics for shaping the capsular sac and responding to zonular tensioning forces, a resilient gel-like shape memory polymer 745 can be used to define a memory shape that occupies a substantial peripheral portion of the capsular sac as in implant 700A of FIG. 25. Still, the shape memory polymer can be compacted to a temporary shape and rolled or folded as in FIG. 17. The fluid media M within the peripheral chamber(s) 722A and optic chamber 722B is non-compressible and accounts for the bulk of the implant that is introduced by an injector through the cornea into the capsular sac. FIG. 25 illustrates an implant device 700A that has a posterior lens that is adaptive in power by exchange of fluid media M between peripheral chamber 722A in peripheral portion 724 and central chamber 722B of lens 720 via channels 740. It can easily be seen from FIG. 25 that fluid can be selectively displaced from the periphery to the center when the respective volumes of the peripheral and central chamber portions are altered upon zonular tensioning and de-tensioning. The embodiment of FIG. 25 operates as the device of FIGS. 16A-16B with induced fluid flows adapted to deform the surface 725 of the adaptive lens 720.

Figure 26:
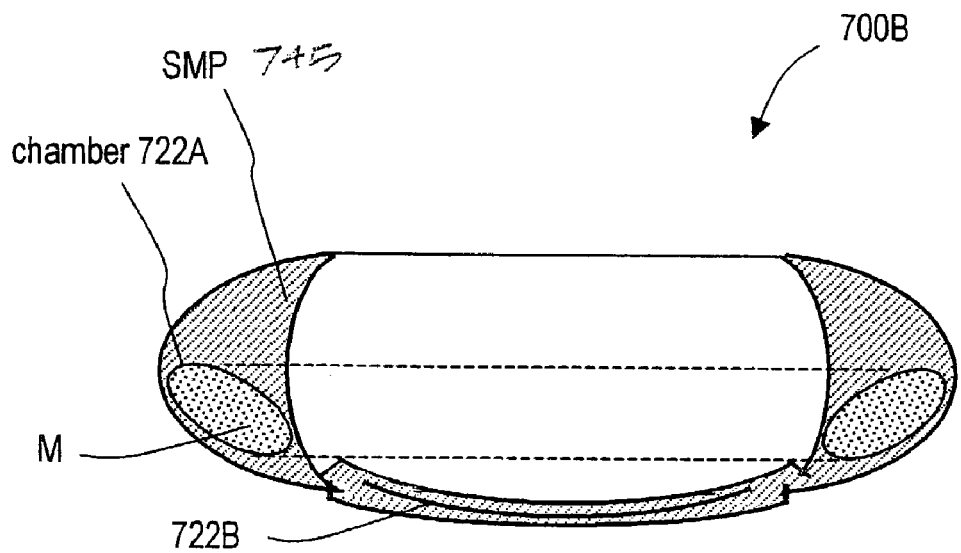
FIGS. 26 is a sectional view of an alternative intracapsular implant and adaptive optic similar to that of FIG. 25 with alternative interior chamber locations.
Figure 27:
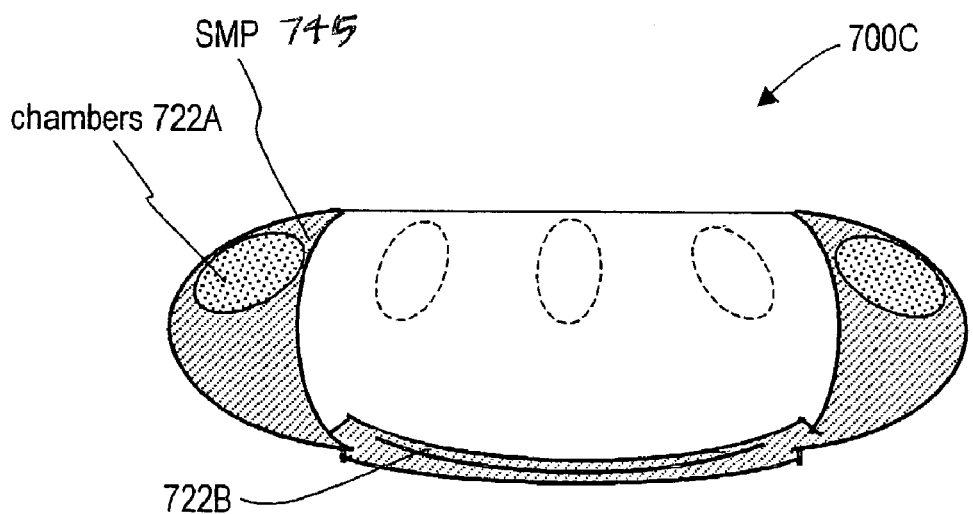
FIGS. 27 is a sectional view of an alternative intracapsular implant and adaptive optic similar to that of FIG. 26.
Figure 28:
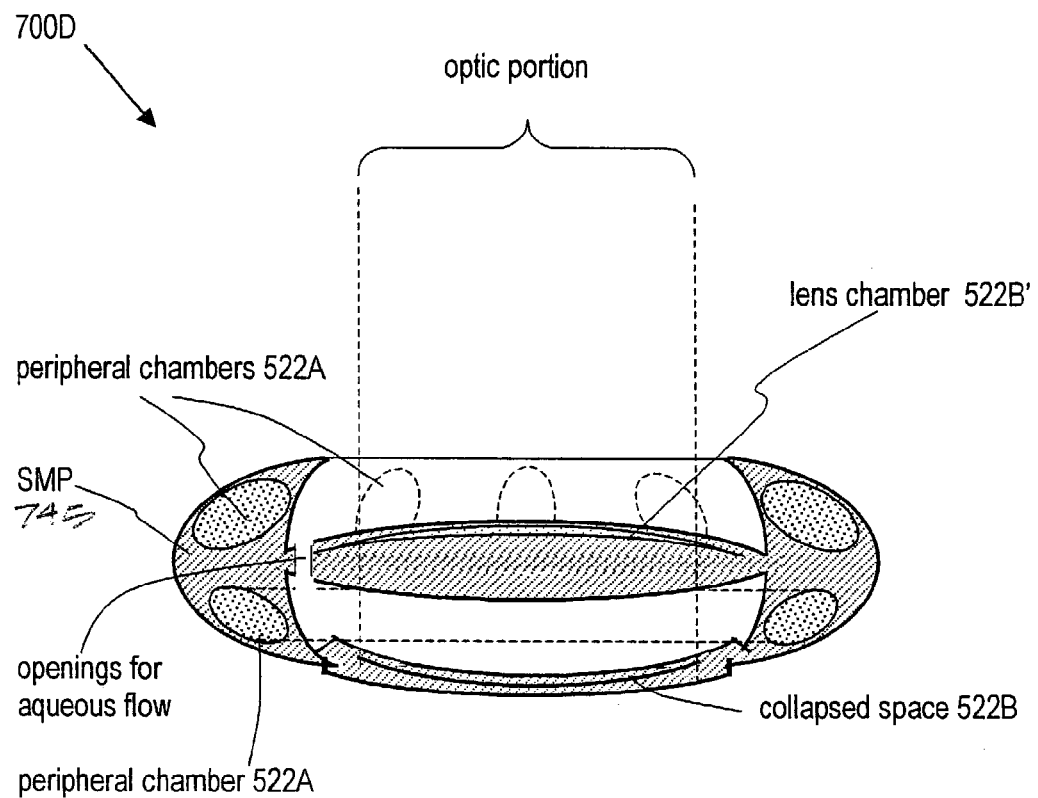
FIGS. 28 is a sectional view of an alternative intracapsular implant with first and second adaptive optic elements that is similar to that of FIG. 25.

FIGS. 26, 27 and 28 illustrate similar embodiments 700B, 700C and 700D that have peripheral chamber(s) 722A in various locations within the peripheral body for different strategies in collapsing the interior chamber(s) 722A therein to enable the adaptive optic. It can be understood that the interior chambers can be annular or spaced apart, or any combination thereof and be located in various portions of the implant periphery. The peripheral chambers can be in equatorial, posterior or anterior portions of the body periphery to alter the power of a single lens or two spaced apart lenses. The fluid flow channels to the lens are not shown for convenience. As shown in FIG. 28, the lens has anterior andl posterior optic surfaces (viewed along the optical axis) arranged such that the anterior-most portion of the anterior optic surface is disposed along the optic axis posterior to the anterior-most portion of the non-optic portion.

Those skilled in the art will appreciate that the exemplary systems, combinations and descriptions are merely illustrative of the invention as a whole, and that variations in the dimensions and compositions of invention fall within the spirit and scope of the invention. Specific characteristics and features of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. An accommodating intraocular lens, comprising:
   a central optic portion, the central optic portion comprising a lens having an optical axis, the lens comprising anterior and posterior optic surfaces through which the optical axis passes wherein at least one optic surface is deformable for altering optic power;
   a peripheral non-optic portion, the non-optic portion comprising an anterior-most portion; and
   a flowable media,
   wherein the non-optic portion is configured for engagement of the interior of a lens capsule, and is adapted to deform in response to a lens capsule shape change due to ciliary muscle movement to move the flowable media from the non-optic portion to the optic portion, and wherein an anterior-most portion of the anterior optic surface is disposed along the optical axis posterior to the anterior-most portion of the non-optic portion.

2. An accommodating intraocular lens as in claim 1 wherein the non-optic portion is at least partly a shape memory polymer.

3. An accommodating intraocular lens as in claim 1 wherein the flowable media is disposed annularly about the optical axis of the optic portion.

4. An accommodating intraocular lens as in claim 1 wherein the flowable media is at least one of a polymer and a fluid.

5. An accommodating intraocular lens, comprising:
   a central optic portion having an optical axis, wherein the optic portion comprises anterior and posterior optic surfaces through which the optical axis passes, and wherein at least a portion of the optic portion is adapted to be deformed to change the power of the intraocular lens; and
   a peripheral non-optic portion, the peripheral portion comprising an anterior-most portion, wherein the peripheral portion is configured for engagement of the interior of a lens capsule, and wherein the peripheral portion is adapted to deform in response to a lens capsule shape change due to ciliary muscle movement, and
   wherein an anterior-most portion of the anterior optic surface is disposed along the optical axis and is disposed posterior to the anterior-most portion of the non-optic portion, and
   wherein the peripheral portion is not disposed along the optical axis.

6. The accommodating intraocular lens as in claim 5 further comprising a flowable media, wherein the non-optic portion is adapted to deform in response to a lens capsule shape change due to ciliary muscle movement to move the flowable media from the non-optic portion to the optic portion to deform the optic portion.

7. The intraocular lens of claim 6 wherein the flowable media has substantially the same index of refraction as the anterior and posterior optic surfaces.

8. The intraocular lens of claim 1 wherein the at least one optic surface that is adapted to be deformed is adapted to be deformed in response to the movement of the flowable media from the non-optic portion to the optic portion.

9. The intraocular lens of claim 8 wherein the anterior optic surface is adapted to be deformed in response to the movement of the flowable media from the non-optic portion to the optic portion to change the power of the lens.

10. The intraocular lens of claim 1 wherein the non-optic portion comprises a first flowable media chamber, wherein the optic portion comprises a second flowable media chamber, and wherein the first and second chambers are in communication to allow the flowable media to move from the non-optic portion to the optic portion.

11. The intraocular lens of claim 1 wherein the flowable media has substantially the same index of refraction as the anterior and posterior optic surfaces of the optic portion.

12. The intraocular lens of claim 1 wherein the non-potion comprises a plurality of haptics extending peripherally from the optic portion.

13. The intraocular lens of claim 5 wherein the non-optic portion comprises a first flowable media chamber, wherein the optic portion comprises a second flowable media chamber, and wherein the first and second chambers are in communication to allow a flowable media to be moved from the first chamber towards the second chamber in response to deformation of the non-optic portion in response to a lens capsule shape change due to ciliary muscle movement.

14. The intraocular lens of claim 5 wherein the portion of the optic portion that is adapted to be deformed to change the power of the intraocular lens comprises the anterior optic surface.

15. The intraocular lens of claim 5 wherein the non-optic portion comprises a plurality of haptics extending peripherally from the optic portion.

16. The intraocular lens of claim 1 wherein the central optic portion comprises an optic chamber, and wherein the non-optic portion comprises a non-optic portion chamber, wherein the chambers are in communication, and wherein the flowable media is movable between the non-optic portion chamber and the optic portion chamber in response to deformation of the non-optic portion,
  wherein an anterior-most portion of the optic chamber is disposed posterior to an anterior-most portion of the non-optic portion chamber.

17. The intraocular lens of claim 16 wherein the anterior-most portion of the anterior optic surface is disposed posterior to the anterior-most portion of the non-optic portion chamber.

18. The intraocular lens of claim 6 wherein the central optic portion comprises an optic chamber, and wherein the non-optic portion comprises a non-optic portion chamber, wherein the chambers are in communication, and wherein the flowable media is movable between the non-optic portion chamber and the optic portion chamber in response to deformation of the non-optic portion,
  wherein an anterior-most portion of the optic chamber is disposed posterior to an anterior-most portion of the non-optic portion chamber.

19. The intraocular lens of claim 18 wherein the anterior-most portion of the anterior optic surface is disposed posterior to the anterior-most portion of the non-optic portion chamber.

* * * * *